United States Patent
Bessette et al.

(10) Patent No.: US 9,247,751 B2
(45) Date of Patent: Feb. 2, 2016

(54) PESTICIDAL COMPOSITIONS CONTAINING ROSEMARY OIL AND WINTERGREEN OIL

(71) Applicant: EcoSMART Technologies, Inc., Roswell, GA (US)

(72) Inventors: Steven M. Bessette, San Clemente, CA (US); A. David Lindsay, Franklin, TN (US)

(73) Assignee: Kittrich Corporation, Pomona, CA (US)

( * ) Notice: Subject to any disclaimer, the term of this patent is extended or adjusted under 35 U.S.C. 154(b) by 0 days.

(21) Appl. No.: 14/309,860

(22) Filed: Jun. 19, 2014

(65) Prior Publication Data

US 2015/0132413 A1  May 14, 2015

Related U.S. Application Data

(60) Division of application No. 13/755,958, filed on Jan. 31, 2013, now Pat. No. 8,877,219, which is a division of application No. 12/872,725, filed on Aug. 31, 2010, now abandoned, which is a division of application No. 11/746,927, filed on May 10, 2007, now abandoned, which is a continuation of application No. 10/014,797, filed on Dec. 14, 2001, now abandoned, which is a continuation-in-part of application No. 09/604,082, filed on Jun. 27, 2000, now abandoned, and a continuation-in-part of application No. 09/505,680, filed on Feb. 17, 2000, now abandoned, and a continuation of application No. 09/340,391, filed on Jun. 28, 1999, now Pat. No. 6,986,898.

(60) Provisional application No. 60/140,845, filed on Jun. 28, 1999, provisional application No. 60/094,463, filed on Jul. 28, 1998, provisional application No. 60/100,613, filed on Sep. 16, 1998, provisional application No. 60/122,803, filed on Mar. 3, 1999.

(51) Int. Cl.

| | | |
|---|---|---|
| A01N 65/00 | (2009.01) | |
| A01N 65/22 | (2009.01) | |
| A01N 25/32 | (2006.01) | |
| A01N 31/04 | (2006.01) | |
| A01N 31/08 | (2006.01) | |
| A01N 31/14 | (2006.01) | |
| A01N 31/16 | (2006.01) | |
| A01N 37/02 | (2006.01) | |
| A01N 37/32 | (2006.01) | |
| A01N 43/30 | (2006.01) | |
| A01N 49/00 | (2006.01) | |
| A01N 53/00 | (2006.01) | |
| A01N 61/00 | (2006.01) | |
| A01N 65/16 | (2009.01) | |
| A01N 65/28 | (2009.01) | |
| A01N 37/40 | (2006.01) | |
| A01N 65/08 | (2009.01) | |
| A01N 65/18 | (2009.01) | |
| A01N 65/20 | (2009.01) | |
| A01N 65/24 | (2009.01) | |

(52) U.S. Cl.
CPC ............... *A01N 65/22* (2013.01); *A01N 25/32* (2013.01); *A01N 31/04* (2013.01); *A01N 31/08* (2013.01); *A01N 31/14* (2013.01); *A01N 31/16* (2013.01); *A01N 37/02* (2013.01); *A01N 37/32* (2013.01); *A01N 37/40* (2013.01); *A01N 43/30* (2013.01); *A01N 49/00* (2013.01); *A01N 53/00* (2013.01); *A01N 61/00* (2013.01); *A01N 65/00* (2013.01); *A01N 65/08* (2013.01); *A01N 65/16* (2013.01); *A01N 65/18* (2013.01); *A01N 65/20* (2013.01); *A01N 65/24* (2013.01); *A01N 65/28* (2013.01)

(58) Field of Classification Search
CPC ....................................................... A61K 36/00
USPC .......................................................... 424/725
See application file for complete search history.

(56) References Cited

U.S. PATENT DOCUMENTS

| | | |
|---|---|---|
| 2,423,284 A | 7/1947 | Babbini |
| 2,945,782 A | 7/1960 | Schraufstatter et al. |
| 3,445,565 A | 5/1969 | Locher et al. |
| 3,761,584 A | 9/1973 | McGovern et al. |
| 4,053,595 A | 10/1977 | Zeck et al. |
| 4,195,080 A | 3/1980 | Herrera et al. |
| 4,308,279 A | 12/1981 | Smeltz |
| 4,368,207 A | 1/1983 | Lover et al. |
| 4,376,784 A | 3/1983 | Harney et al. |
| 4,379,168 A | 4/1983 | Dotolo |
| 4,759,930 A | 7/1988 | Granirer et al. |
| 4,818,534 A | 4/1989 | Levy |
| 4,910,205 A | 3/1990 | Kogan et al. |
| 4,948,013 A | 8/1990 | Thomas et al. |

(Continued)

FOREIGN PATENT DOCUMENTS

| | | |
|---|---|---|
| BE | 1002598 A | 4/1991 |
| CA | 2077284 A | 2/1994 |

(Continued)

OTHER PUBLICATIONS

King, W.V., "Chemicals Evaluated as Insecticides and Repellents at Orlando, Fla.," Agriculture Handbook No. 69, May 1954.

(Continued)

*Primary Examiner* — Michael Meller
(74) *Attorney, Agent, or Firm* — Nixon & Vanderhye, P.C.

(57) ABSTRACT

Pesticidal compositions containing plant essential oils, such as rosemary oil and/or wintergreen oil, and methods for using same are disclosed.

3 Claims, 13 Drawing Sheets

(56) References Cited

U.S. PATENT DOCUMENTS

| | | |
|---|---|---|
| 4,983,389 A | 1/1991 | Levy |
| 4,983,390 A | 1/1991 | Levy |
| 4,985,251 A | 1/1991 | Levy |
| 4,999,187 A | 3/1991 | Vernon |
| 5,004,596 A | 4/1991 | Cocherell et al. |
| 5,013,769 A | 5/1991 | Murray et al. |
| 5,215,757 A | 6/1993 | El-Nokaly |
| 5,227,163 A | 7/1993 | Eini et al. |
| 5,246,919 A | 9/1993 | King |
| 5,248,503 A | 9/1993 | Emanuel-King |
| 5,288,483 A | 2/1994 | Cardin et al. |
| 5,330,771 A | 7/1994 | Barkalow et al. |
| 5,403,587 A | 4/1995 | McCue et al. |
| 5,439,690 A | 8/1995 | Knight |
| 5,496,857 A | 3/1996 | Targosz |
| 5,688,509 A | 11/1997 | Radwan et al. |
| 5,693,344 A | 12/1997 | Knight et al. |
| 5,711,937 A | 1/1998 | Nishida et al. |
| 5,783,202 A | 7/1998 | Tomlinson et al. |
| 5,800,897 A | 9/1998 | Sharma et al. |
| 5,849,317 A | 12/1998 | Shorey et al. |
| 5,858,383 A | 1/1999 | Precopio |
| 5,888,984 A | 3/1999 | Brown |
| 5,948,743 A | 9/1999 | Fonsny et al. |
| 6,004,569 A | 12/1999 | Bessette et al. |
| 6,114,384 A | 9/2000 | Bessette et al. |
| 6,183,767 B1 | 2/2001 | Bessette et al. |
| 6,230,435 B1 | 5/2001 | Carman |
| 6,231,865 B1 | 5/2001 | Hsu et al. |
| 6,531,163 B1 | 3/2003 | Bessette et al. |
| 6,689,397 B2 | 2/2004 | Clark et al. |
| 6,884,763 B2 | 4/2005 | Willard et al. |
| 6,974,584 B2 | 12/2005 | Bessette |
| 6,986,898 B1 | 1/2006 | Bessette |
| 2002/0022043 A1 | 2/2002 | Miller |
| 2002/0131986 A1 | 9/2002 | Clark et al. |
| 2003/0194454 A1 | 10/2003 | Bessette et al. |
| 2005/0214337 A1 | 9/2005 | McGee et al. |
| 2007/0098750 A1 | 5/2007 | Bessette |
| 2007/0207221 A1 | 9/2007 | Bessette et al. |
| 2008/0038383 A1 | 2/2008 | Bessette et al. |
| 2008/0269177 A1 | 10/2008 | Bessette |

FOREIGN PATENT DOCUMENTS

| | | |
|---|---|---|
| CA | 2099929 | 7/1994 |
| DE | 524 383 | 6/1931 |
| DE | 3526911 A | 3/1986 |
| DE | 3717467 A | 12/1988 |
| DE | 3733640 A | 4/1989 |
| DE | 19631594 A | 2/1998 |
| EP | 0 262 885 A2 | 4/1988 |
| EP | 462 347 | 12/1991 |
| EP | 0 495 684 A1 | 7/1992 |
| EP | 0 557 174 A1 | 8/1993 |
| EP | 0 635 208 A1 | 1/1995 |
| EP | 0 894 435 A1 | 2/1999 |
| EP | 0945966 | 9/1999 |
| EP | 1 048 293 A1 | 11/2000 |
| FR | 2 553 664 A | 4/1985 |
| FR | 2 759 546 A | 8/1998 |
| GB | 1 593 601 A | 7/1981 |
| GB | 1 604 859 A | 12/1981 |
| GB | 2 232 354 A | 12/1990 |
| GB | 2 267 643 A | 12/1993 |
| JP | A 55104202 | 8/1980 |
| JP | 1-130415 | 5/1989 |
| JP | 3-127702 | 5/1991 |
| JP | 4308510 | 10/1992 |
| JP | 06 107505 | 4/1994 |
| JP | 53 034919 | 4/1995 |
| JP | 07145598 | 6/1995 |
| JP | 11060421 | 3/1999 |
| WO | WO 91/05561 | 5/1991 |
| WO | WO95/07024 | 3/1995 |
| WO | WO99/52359 | 10/1995 |
| WO | WO 96/20594 | 7/1996 |
| WO | WO 97/07677 | 3/1997 |
| WO | WO 98/04128 | 2/1998 |
| WO | WO 98/27812 | 7/1998 |
| WO | WO98/30124 | 7/1998 |
| WO | WO98/49901 | 11/1998 |
| WO | WO98/54971 | 12/1998 |
| WO | WO 99/37148 | 7/1999 |
| WO | WO 00/00213 | 1/2000 |
| WO | WO 00/05964 | 2/2000 |
| WO | WO 01/00032 | 1/2001 |
| WO | WO 01/00034 | 1/2001 |
| WO | WO 01/13726 A1 | 3/2001 |
| WO | WO 02/098439 | 12/2002 |

OTHER PUBLICATIONS

Database WPI, Derwent Publications, Ltd., London, GB, "Insecticial Composition Contains Plant Oil and/or Terpene Oil to Improve Insecticidal Effect" (JP 308510).

"FIFRA Section 25(b) Exemptions, Regulatory Relief Proposed", Pesticide and Toxic Chemical News, PROMT Full Text Article, pp. 1-3 (1994).

Chemical Abstracts 119(5): 43357q (1993).

Hori, M., "Repellency of Rosemary Oil against Myzus Persicae in Laboratory and in the Screenhouse", J. Chemical Ecology, vol. 24, No. 9, 1998, pp. 1425-1433.

Merck Index. The Twelfth Edition. 1996. Nos. 1162, 3947, 7625-7626 at pp. 661. 185, 7726.

Coats, Joel et al., "Toxicity and Neurotoxic Effects of Monoterpeniods in Insects and Earthworms", ACS. Symp. Ser. (1991), 449 (Nat. Occuring Pest Bioregul.) 305-16.

Karr, L.L. et al. "Effects of Four Monoterpeniods on the Growth and Reproduction of the German Cockroach", J. Pestic. Science, vol. 85, No. 2, 1992, pp. 424-429.

Inazuka, S., "New Methods of Evaluation for Cockroach Repellents and Repellency of Essential Oils Against German Cockroach (Blatella germanica)", J. Pestic. Science, vol. 7, 1982, pp. 133-134.

Inazuka, S., "Cockroaches Repellents Contained in Oils of Japanese Mint and Scotch Spearmint", J. Pestic. Science, vol. 7, 1982, pp. 145-154.

Pfeffermuinzol, 1996 Deutsches Arzneibuch XP002150746.

Rompps Chemie Lexikon, "Rosmarinol", 1992, Geoge_Thieme-Verlag, Stuttgart, Germany p. 3921.

Casida, John E. "Pyrethrum" pp. 26-27, 30-31, 88-91, 196-199, 276, 202-203, 267 Academic Press 1973.

Vartak et al., "Comparative Repellent Properties of Certain Chemicals Against Mosquitoes, House Flies and Cockroaches Using Modified Techniques"; J. Com. Dis., 26 (3): 156-160, 1994.

Kuhr et al. Mechanism of Pesticide Action; 1974, American Chemical Society, p. 39.

Ngoh, Shay, et al., "Insecticidal and Repellent Properties of Nine Volatile Constituents of Essential Oils Against the American Cockroach", Periplaneta americana (L.), Pesticide Science, vol. 54, No. 3, Nov. 1998.

Singh, K. et al., "Synergism of Mkg-264 and Piperonly Butoxide on the Toxicity of Plant Derived", Database CHEMABS 'Online!, Chemical Abstracts Service, Coiumbus, OH, vol. 36, No. 15, pp. 3055-3060, 1998.

Maffia, A. J., Abstract, Database WPI, Section Ch, Week 199412, Derwent Publications Ltd., London, GB, AN 1994-092916, XP002133730, CA2099929. Jan. 7, 1994.

Watanabe et al., "Killing activities of the volatiles emitted from essential oils for Dermatophagoides pteronyssinus, Dermatophagoides farinae and Tyrophagus putrescentiae", Shoyakugaku Zasshi, 43(2):163-168 (1989).

Merk Index Encyclopedia of Chemicals, Drugs and Biologicals, 12th edition. 1996 pp. 113, 177-179, 189, 393, 717, 718, 938, 963, 1237, 1247, 1281, 1431, 1641, 1642.

Fehr et al., "Studies on the shelf life of peppermint leaves, rosemary leaves and thyme." Pharmazeutishe Zeitung, 124(46), 2342-2349 (1979).

(56) References Cited

OTHER PUBLICATIONS

Elamrani et al., "A Study of Moroccan Rosemary Oils", *J. Essent. Oil Res.*, 12:487-495 (2000).

Caccioni et al., "Inhibition of Germination and Growth of Fruit and Vegetable Postharvest Pathogenic Fungi by Essential Oil Components," *J. Essent. Oil Res.*, 6:173-179 (1994).

Chermenskaya, T.D., et al., "Behavioural Responses of Western Flower Thrips, *Frankliniella occidentalis* (Pergande), to Volatiles from Three Aromatic Plants," *Insect Sci. Applic.*, 21(1)67-72 (2001).

Mauch-Mani et al., "Salicylic Acid and Systemic Acquired Resistance to Pathogen Attack," *Annals of Botany*, 82:535-540 (1998).

Hardie et al., "Methyl Salicylate and (—)-(1$R$,5$S$)-Myrtenal are Plant-derived Repellents for Black Bean Aphid, *Aphis fabae* SCOP. (Homoptera: Aphididae), " *Journal of Chemical Ecology*, 20(11):2847-2855 (1994).

Koschier et al., "Influence of Plant Volatiles on Feeding Damage caused by the onion thrips *Thrips tabaci*," *Crop Protection*, 21:419-425 (2002).

Borden et al., "Potential for Nonhost Volatiles as Repellents in Integrated Pest Management of Ambrosia Beetles," *Integrated Pest Management Reviews*, 6:221-236 (2001).

Markovic et al., "Volatiles Involved in the Nonhost Rejection of *Fraxinus pennsylvanica* by *Lymantria dispar* Larvae," *J. Agri. Food Chem.*, 44(3):932-938 (1996).

Lu et al., http://www.apsnet.org/meetings/abstract/1999/c99ab26.htm, "Methyl Salicylate Induced Resistance of Tomato to *Xanthomonas campestris* pv. *Vesticatoria*," Abstract (1999).

Zhou et al., "Repellent Effects of Herbivore-induced Rice Volatiles on the Brown Planthopper, *Nilaparvata lugens* Stål,"*Acta Entomologica Sinica*, 46(6):739-744 (2003) Chinese Language With English Abstract.

PESTICIDAL COMPOSITIONS CONTAINING ROSEMARY OIL AND WINTERGREEN OIL

CROSS-REFERENCE TO RELATED APPLICATIONS

This continuing application is a divisional of U.S. application Ser. No. 13/755,958, filed Jan. 31, 2013, which is a divisional of U.S. application Ser. No. 12/872,725, filed Aug. 31, 2010, which is a divisional of U.S. application Ser. No. 11/746,927, filed May 10, 2007, which is a continuation of U.S. application Ser. No. 10/014,797, filed Dec. 14, 2001, which (1) is a continuation-in-part of U.S. application Ser. No. 09/604,082, filed Jun. 27, 2000, which claims the benefit of U.S. Provisional Application Ser. No. 60/140,845, filed Jun. 28, 1999, the entire disclosure of which is incorporated herein by reference, (2) is a continuation-in-part of U.S. application Ser. No. 09/505,680, filed Feb. 17, 2000, the entire disclosure of which is incorporated herein by reference and (3) is a continuation-in-part of U.S. application Ser. No. 09/340,391, filed Jun. 28, 1999, now U.S. Pat. No. 6,986,898, which in turn claims the benefit of U.S. Provisional Patent Application No. 60/094,463, filed Jul. 28, 1998, U.S. Provisional Patent Application Ser. No. 60/100,613, filed Sep. 16, 1998, and U.S. Provisional Patent Application Ser. No. 60/122,803, filed Mar. 3, 1999, the entire disclosures of each of the above-referenced patent applications are incorporated herein by reference. For avoidance of doubt, this continuing application claims the benefit of each of the above-identified patent applications.

FIELD OF THE INVENTION

The present invention relates to novel pesticidal compositions and methods for using same for the control of pests.

BACKGROUND OF THE INVENTION

Pests are annoying to humans for several reasons. Pests include pathogenic organisms which infest mammals and plants; some pests can spread disease as disease vectors. The pathogenic organisms that infest plants and cause economic loss of plant crops include fungi, insects, arachnids, gastropods, nematodes and the like. The pathogenic organisms that infest animals include ticks, mites, fleas, and mosquitoes. Other pests include cockroaches, termites and ants. These and other pests have annually cost humans billions of dollars in crop losses in the case of agricultural pests and in the expense of keeping them under control. For example, the losses caused by pests in agricultural environments include decreased crop yield, reduced crop quality, and increased harvesting costs. In household scenarios, insect pests may act as vectors for diseases and allergic matter.

Over the years, synthetic chemical pesticides have provided an effective means of pest control. For example, one approach teaches the use of complex, organic insecticides, such as disclosed in U.S. Pat. Nos. 4,376,784 and 4,308,279. Other approaches employ absorbent organic polymers for widespread dehydration of the insects. See, U.S. Pat. Nos. 4,985,251; 4,983,390; 4,818,534; and 4,983,389. Use of inorganic salts as components of pesticides has also been tried, as disclosed in U.S. Pat. Nos. 2,423,284 and 4,948,013, European Patent Application No. 462 347, Chemical Abstracts 119(5):43357q (1993) and Farm Chemicals Handbook, page c102 (1987).

However, it has become increasingly apparent that the widespread use of synthetic chemical pesticides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Moreover, some target pests have even shown an ability to develop resistance to many commonly used synthetic chemical pesticides. In recent times, regulatory guidelines have encouraged a search for potentially less dangerous pesticidal compositions via stringent restrictions on the use of certain synthetic pesticides. As a result, elimination of effective pesticides from the market has limited economical and effective options for controlling pests. As an alternative, botanical pesticides are of great interest because they are natural pesticides, i.e., toxicants derived from plants that are safe to humans and the environment. Use of food-grade plant essential oils have been tried, as described in U.S. Pat. Nos. 5,439,690, 5,693,344, 6,004,569, 6,114,384, and 6,183,767 B1. However, these plant essential oils when used alone can be expensive, impractical or ineffective under certain circumstances.

Accordingly, there is a great need for novel pesticidal compositions containing no pyrethrum, synthetic pyrethroids, chlorinated hydrocarbons, organo phosphates, carbamates and the like, but comprising food-grade plant essential oils, to be used against invertebrate pests, including insects, arachnids, larvae and eggs thereof. In addition, there is a need for a method of treating a locus to be protected to kill and repel invertebrate pests.

SUMMARY OF THE INVENTION

A primary object of the present invention is to provide novel pesticidal compositions for use against pests such as invertebrate insects, arachnids, larvae and eggs thereof.

Another object of the invention is to provide novel pesticidal compositions containing rosemary oil and/or wintergreen oil as a contact and repellent pesticide in household applications.

Another object of the invention is to provide novel pesticidal compositions containing rosemary oil and/or wintergreen oil as a contact and repellent pesticide in lawn and garden applications.

Another object of the invention is to provide novel pesticidal compositions containing rosemary oil and/or wintergreen oil as a contact and repellent pesticide in greenhouse and nursery applications.

Another object of the invention is to provide novel pesticidal compositions containing rosemary oil and/or wintergreen oil as a contact and repellent pesticide in agricultural applications.

Another object of the invention is to provide novel pesticidal compositions containing rosemary oil and/or wintergreen oil as a contact pesticide against various stages of the lifecycle of invertebrate pests, including eggs, nymphs, pupae and adults.

Another object of the invention is to provide novel pesticidal compositions containing rosemary oil and/or wintergreen oil that can be used with conventional pesticides, including conventional plant essential oils such as thyme oil, eugenol and 2-phenethyl propionate, and conventional synergists such as piperonyl butoxide.

It is also an object of the present invention to provide a method of treating a locus where invertebrate pest control is desired.

It is also an object of the present invention to provide a pesticidal composition and method for mechanically and neurally controlling invertebrate pests.

It is a further object to provide a safe, pesticidal composition and method that will not harm mammals or the environment.

It is still another object to provide a pesticidal composition and method that has a pleasant scent, but is not too strong or lingering, and that can be applied without burdensome safety precautions.

It is still another object to provide a pesticidal composition and method as described above which can be inexpensively produced or employed.

It is still another object to provide a pesticidal composition and method as described above which can be used indoors and outdoors and will not soften, dissolve, or otherwise adversely affect treated surfaces.

It is still another object to provide a pesticidal composition and method as described above which is exempt from registration with the U.S. Environmental Protection Agency under the Federal Insecticide, Fungicide and Rodenticide Act.

It is still another object to provide a pesticidal compostioin that is non-phytotoxic and can be safely applied to economically valuable plants or crops.

It is still another object to provide a pesticidal composition and method as described above which is exempt from a food tolerance residue requirement when used on food under the Federal Food and Drug Cosmetic Act.

It is still another object to provide a pesticidal composition and method as described above which is allowed in organic farming under the Organic Materials Review Institute and the National Organic Program.

It is yet another object of the invention to provide a pesticidal composition and method to which invertebrate pests can not build resistance.

It is yet another object of the invention to provide a pesticidal composition and method to provide quick knockdown and kill of invertebrate pests, particularly in household applications.

It is yet another object of the invention to provide a pesticidal composition and method as described above that can be formulated as a water-based emulsion, some of which may be exempt from registration with the U.S. EPA.

One or more of the above non-limiting objects and technical effects are accomplished by the present invention, which is directed to pesticidal compositions comprising rosemary oil and/or wintergreen oil. In addition, the present invention is directed to a method for controlling pests by applying a pesticidally-effective amount of the pesticidal compositions of the present invention to a location where pest control is desired. The pesticidal compositions of the represent invention can be applied and used as liquid sprays, crystals, gels, and pellets, impregnating material, such as posts, etc.

As used herein, the term "rosemary oil" denotes both extracted and synthetic versions of *Rosmarinus officinalis, Limonium vulgare, Andromeda polifolia*, and derivatives thereof, having at least one of the following constituents: alpha-terpineol, beta-caryophyllene, borneol, bornyl acetate, bornyl acetate, camphene, camphor, cineole, diosmetin, diosmin, diterpenes, flavonoids including apigenin, genkwanin, hispidulin, isobutyl acetate, limonene, linalool, lutiolin, octanone, phenolic acids (Rosmarinic acid), pinene, saponincineole, sinensetin, terpinen-4-ol, thujone, and/or verbenol.

As used herein, the term "wintergreen oil" (Oil of *Gaultheria procumbens*) denotes both extracted (by distillation of the leaves of *Gaultheria fragrantissima* Wall) and synthetic versions (e.g., methyl salicylate) and derivatives thereof, including, without limitation, O-hydroxybenzoic acid methyl ester; Betula oil; salicylic acid, methyl ester; benzoic acid, 2-hydroxy-, methyl ester (2-HOC$_6$H$_4$COOCH$_3$) (CAS Nos. 119-36-8 and 68917-75-9); sweet birch oil; *Gaultheria* oil; methyl hydroxybenzoate; O-hydroxybenzoate; 2-(methoxycarbonyl)phenol; 2-carbomethoxyphenol; Linsal; methylester kyseliny salicylove (Czech); o-anisic acid; panalgesic; methyl o-hydroxybenzoate; teaberry oil; analgit; exagien; flucarmit; anthrapole nd; Metsal liniment, and the like.

As used herein, the term "pest" refers to organisms and microorganisms, including pathogens, that negatively affect plants or animals by colonizing, attacking or infecting them. This includes organisms that spread disease and/or damage the host and/or compete for host nutrients. In addition, plant pests are organisms known to associate with plants and which, as a result of that association, causes a detrimental effect on the plant's health and vigor. Plant pests include but are not limited to fungi, bacteria, insects, and nematodes.

The term "pesticide" as used herein refers to a substance that can be used in the control of agricultural, natural environmental, and domestic/household pests, such as insects, fungi, bacteria, and viruses. The term "pesticide" is understood to encompass naturally occurring or synthetic chemical insecticides (larvicides, and adulticides), insect growth regulators, acaricides (miticides), nematicides, ectoparasiticides, bactericides, fungicides, and herbicides (substance which can be used in agriculture to control or modify plant growth).

The term "plant" as used herein encompasses whole plants and parts of plants such as roots, stems, leaves and seed, as well as cells and tissues within the plants or plant parts. Target crops to be protected within the scope of the present invention include, without limitation, the following species of plants: cereals (wheat, barley, rye, oats, rice, *sorghum* and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), *citrus* fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

The terms "control" or "controlling" used throughout the specification and claims, are meant to include any pesticidal (killing) or pestistatic (inhibiting, maiming or generally interfering) activities of a pesticidal composition against a given pest. Thus, these terms not only include killing, but also include such activities as those of chemisterilants which produce sterility in insects by preventing the production of ova or sperm, by causing death of sperm or ova, or by producing severe injury to the genetic material of sperm or ova, so that the larvae that are produced do not develop into mature progeny. The terms also include repellant activity that protect animals, plants or products from insect attack by making food or living conditions unattractive or offensive to pests. These repellant activities may be the result of repellents that are poisonous, mildly toxic, or non-poisonous to pests.

The pesticidal compositions of the present invention may be used in the control of agricultural, natural environmental, and domestic/household pests, such as invertebrate insects, arachnids, larvae and eggs thereof, as well as against fungi, bacteria, and viruses.

In one aspect, the present invention relates to pesticidal compositions containing rosemary oil and/or wintergreen oil against household pests including but not limited to cockroaches, ants, flies and spiders.

In another aspect, the present invention relates to pesticidal compositions containing rosemary oil and/or wintergreen oil against plant pests, including but not limited to mites, aphids, *thrips*, whiteflies, loopers, worms, beetles, leafrollers, moths and weevils.

In still another aspect, the present invention relates to pesticidal compositions comprising rosemary oil and/or wintergreen oil to be used as a contact pesticide against invertebrates such as insects, arachnids, larvae and eggs thereof.

In a further aspect, the present invention relates to pesticidal compositions comprising rosemary oil and/or wintergreen oil to be used as a repellent pesticide against invertebrate pests, and provide anti-feedant properties against plant pests in particular.

The present invention also relates to pesticidal compositions comprising rosemary oil and/or wintergreen oil in combination with diluents such as mineral oil (e.g., paraffin oil; liquid petrolatum; white mineral oil; Nujol, alboline; bayol F; blandlube; drakeol; cutting oil; heat-treating oil; hydraulic oil; transformer oil; lubricating oil; drawing oil; crystol 325, CAS Nos. 8012-95-1, 64742-46-7, 39355-35-6, 79956-36-8, 83046-05-3), d-limonene, safflower oil, citronellal and sesame oil.

The present invention further relates to various optimum ratios between and among the constituents of each proprietary blend and the proper delivery system for each blend. For instance, the mixing ratio of rosemary oil to wintergreen oil is the ratio wherein rosemary oil and wintergreen oil show a synergistic effect, and usually is from 100:1 to 1:100 parts by weight, preferably within the range from 13:1 to 1:13.

The present invention also relates to pesticidal compositions containing rosemary oil and/or wintergreen oil that can be used with conventional pesticides. For example, the conventional pesticide may be a member selected from the group consisting of chlorinated hydrocarbon, synthetic pyrethroid, organo phosphate, carbamate, macrolide, insect growth regulator, neonicitinoid, organo-tin, and propargite. Further, conventional pesticide may be a member selected from the group consisting of allethrin, azadirachtin (neem), carbaryl, chlorpyrifos, DDT, fenvalorate, malathion, permethrin, pyrethrum, resmethrin, rotenone and pyrethroid. The conventional pesticide may also be a member selected from the group consisting of pyrethrolone, allethrolone, chrysanthemic acid, chrysanthemyl alcohol, cis-jasmone, and dimethyl sulfoxide (DMSO).

In a further aspect, the present invention relates to a method for controlling invertebrates such as insects, arachnids, larvae and eggs thereof, including but not limited to cockroaches, ants, flies, spiders, mites, aphids, *thrips*, whiteflies, loopers, worms, beetles, leafrollers, moths and weevils, by the application of pesticidally effective amounts of the pesticidal compositions of the present invention to a location where invertebrate pest control is desired.

At least one of the above objects and advantages may be realized and attained by means of the instrumentalities and combinations particularly recited in the appended claims and/or supported by this written description. Additional objects and attendant advantages of the present invention will be set forth, in part, in the description that follows, or may be learned from practicing or using the present invention. It is to be understood that the foregoing general description and the following detailed description are exemplary and explanatory only and are not to be viewed as being restrictive of the invention, as claimed.

BRIEF DESCRIPTION OF THE DRAWINGS

The accompanying drawings, which are incorporated in and constitute a part of the specification, illustrates the present invention and, together with the description, serves to exemplify the principles of the present invention.

DETAILED DESCRIPTION OF PREFERRED EMBODIMENTS

Figure 1:
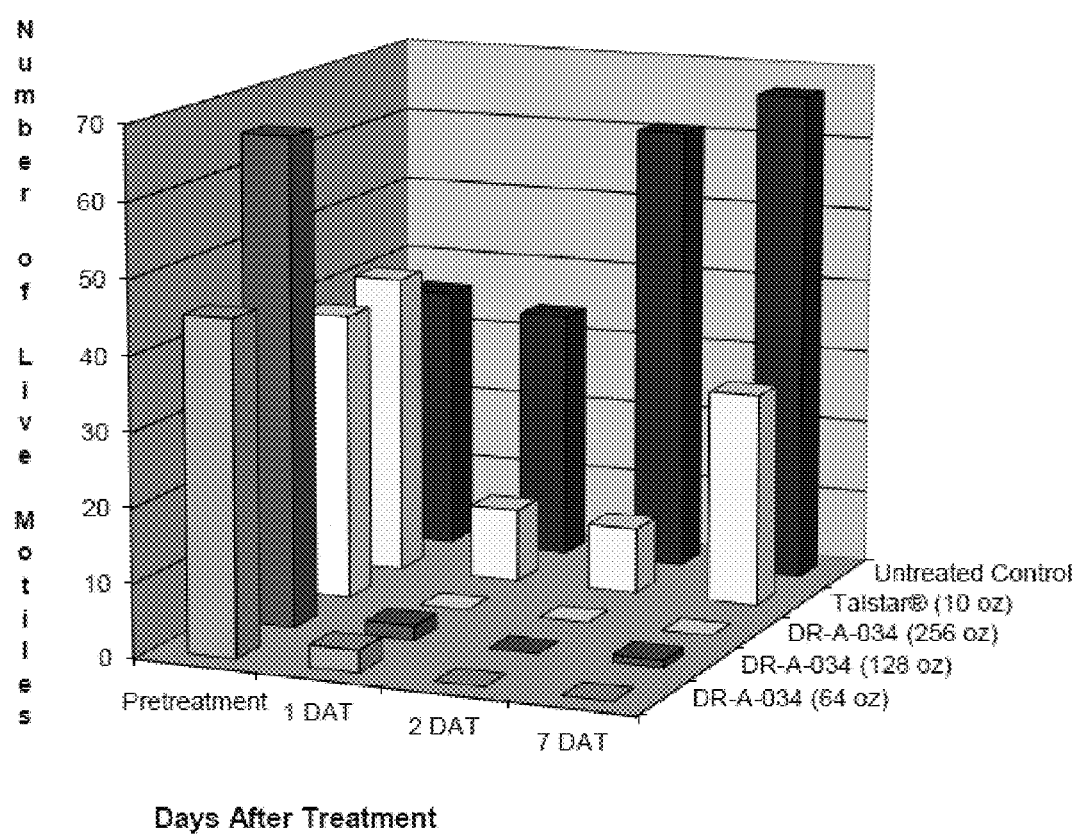
FIGS. 1-11 depict data obtained from comparative studies of HEXACIDE™ (DR-A-034) and conventional pesticides.
Figure 2A:
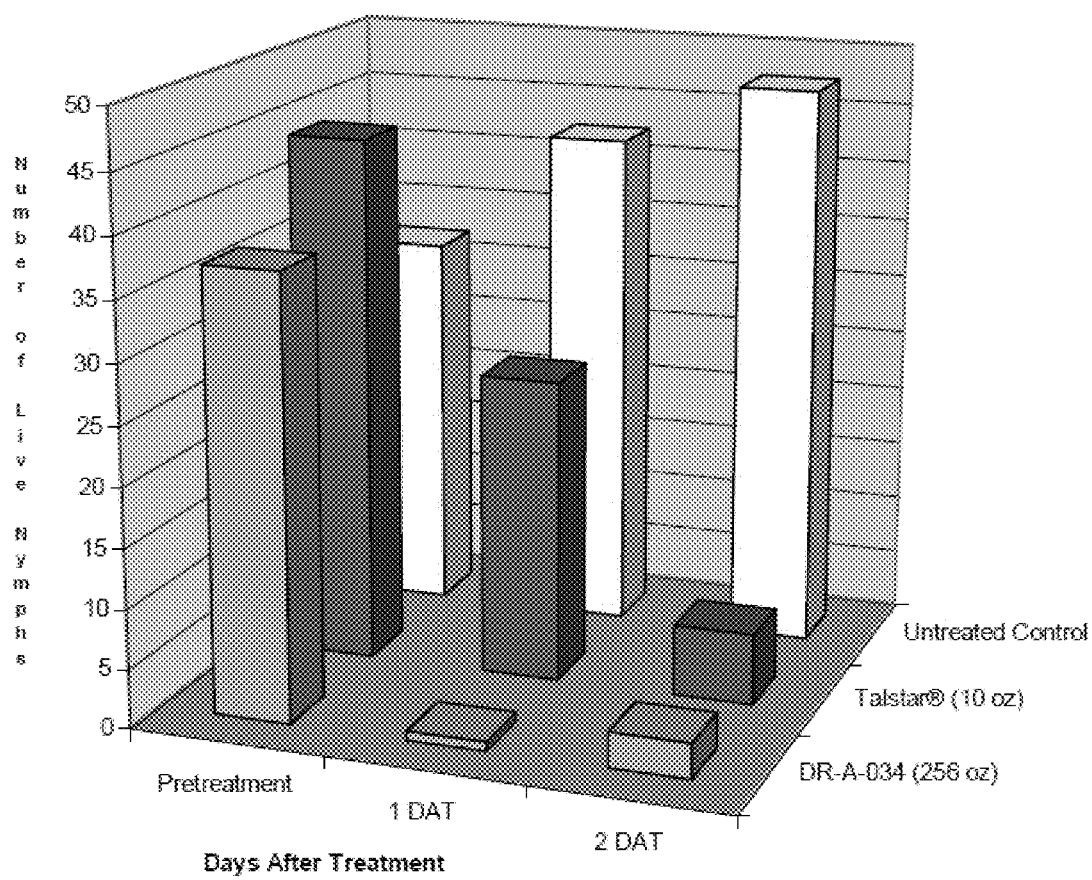
Figure 2B:
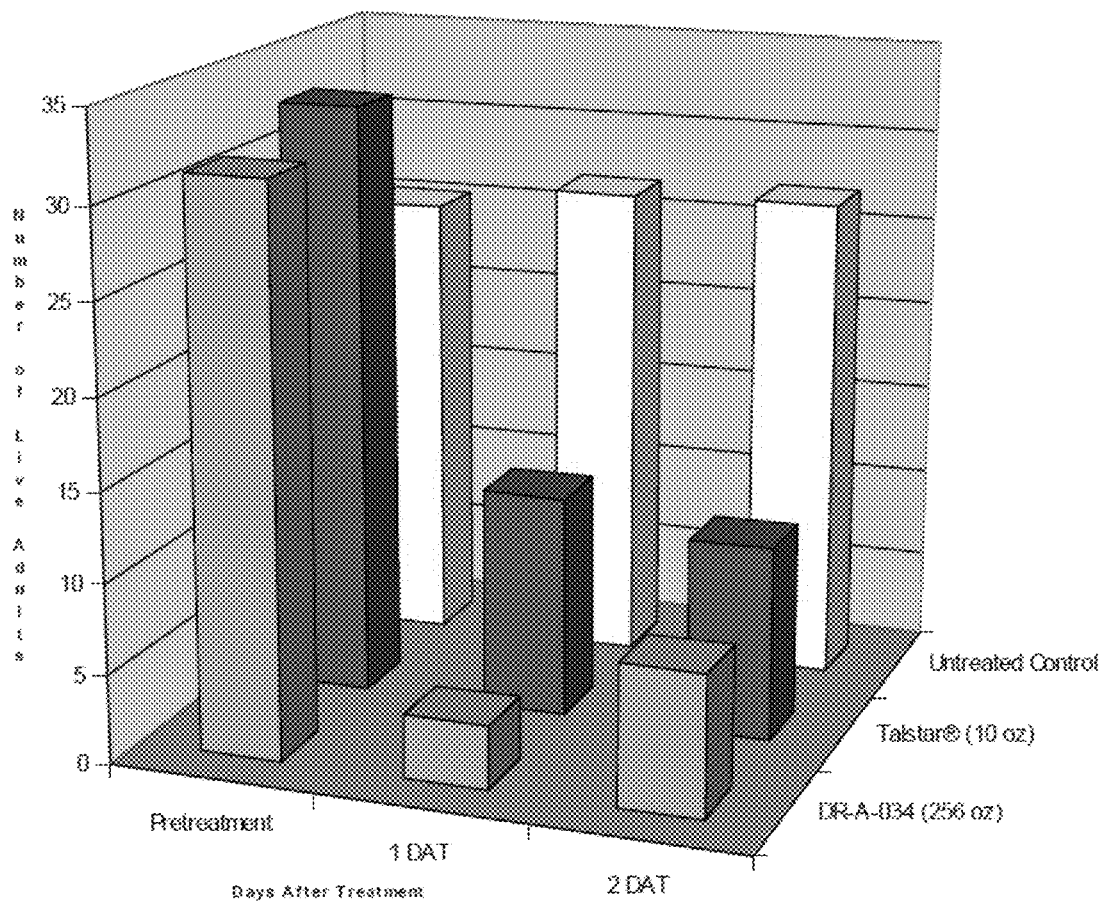
Figure 3:
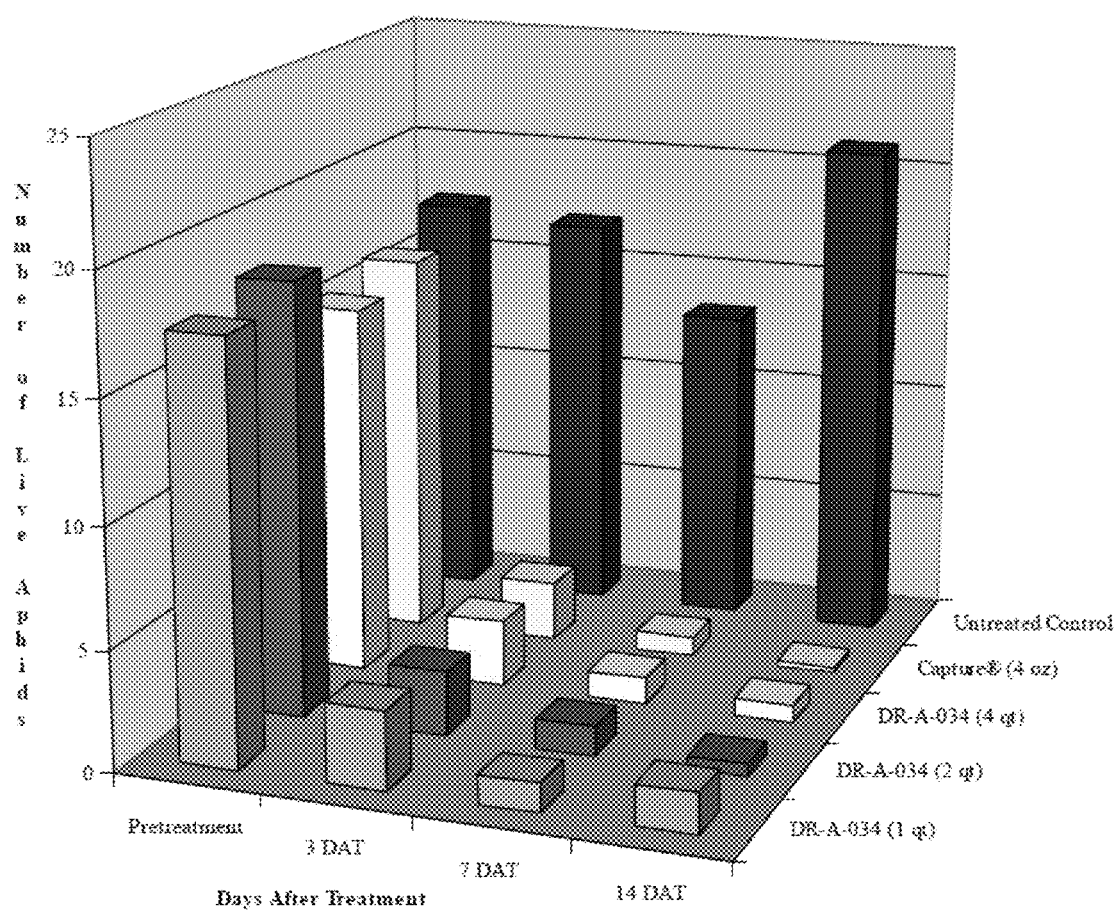
Figure 4:
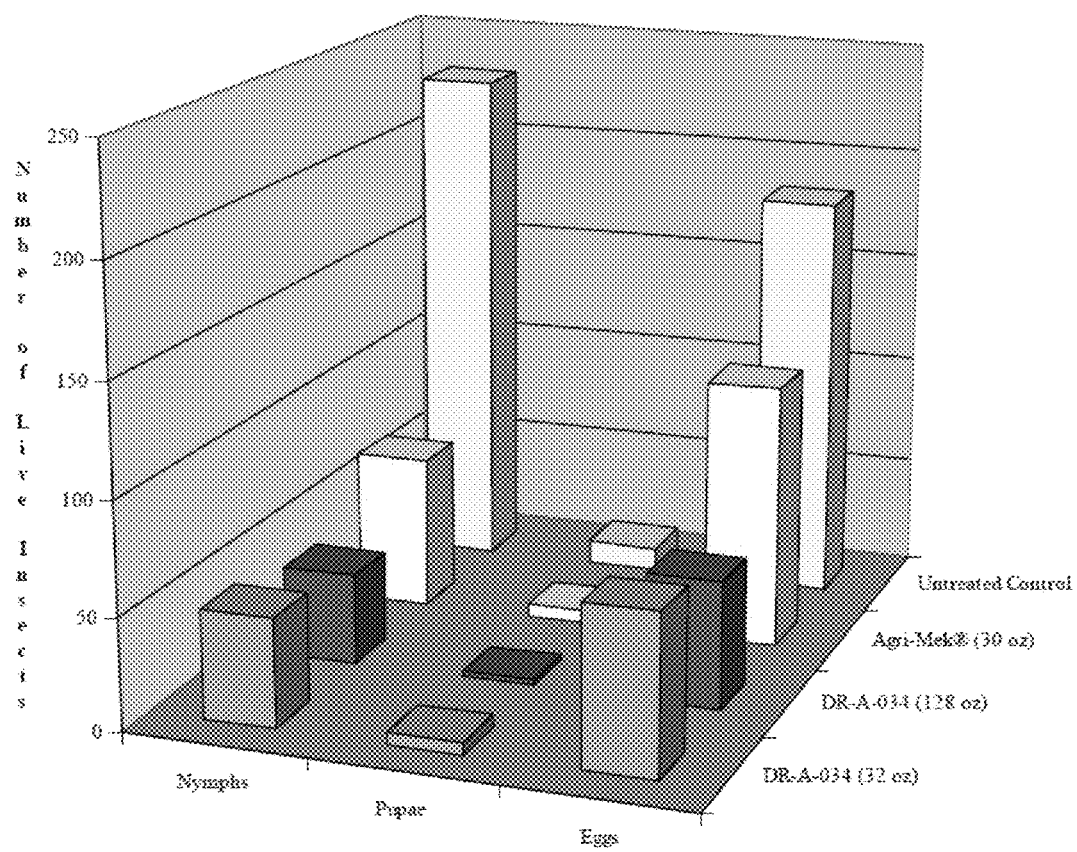
Figure 5:
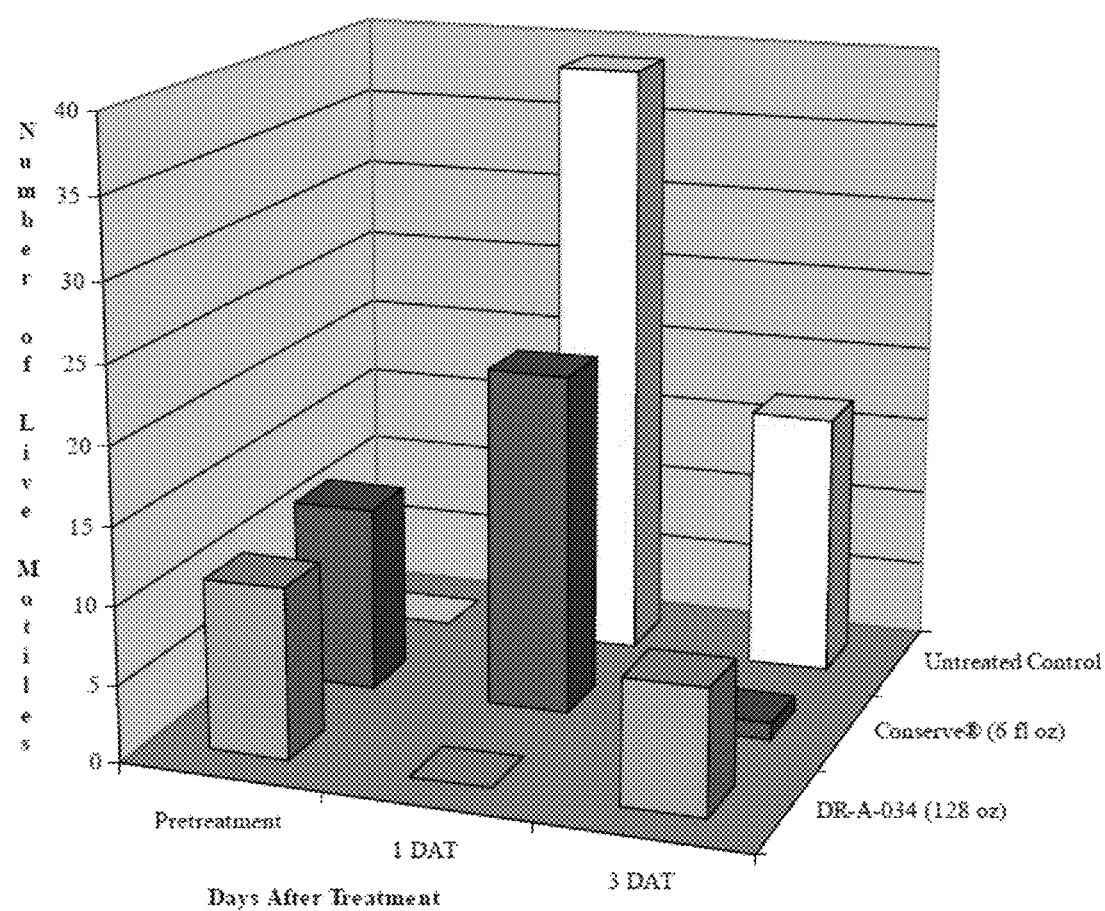
Figure 6:
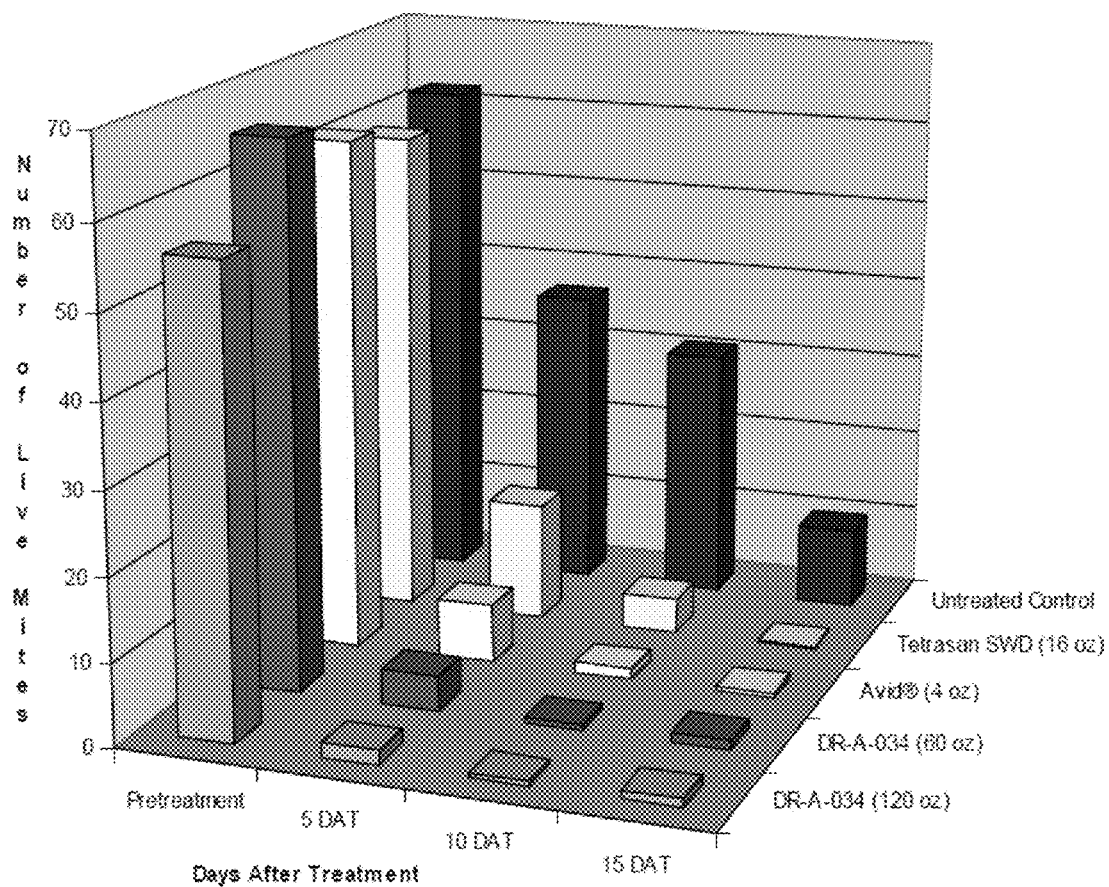
Figure 7:
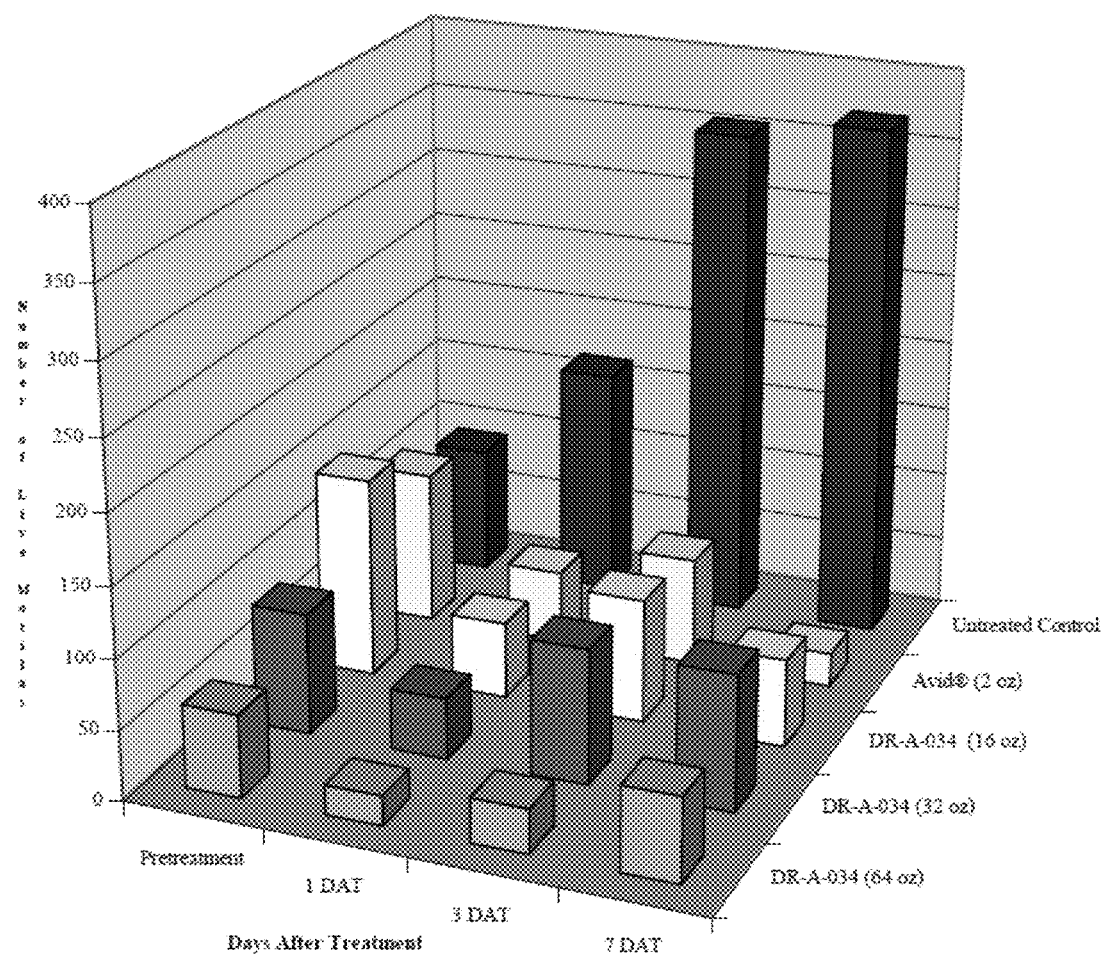
Figure 8:
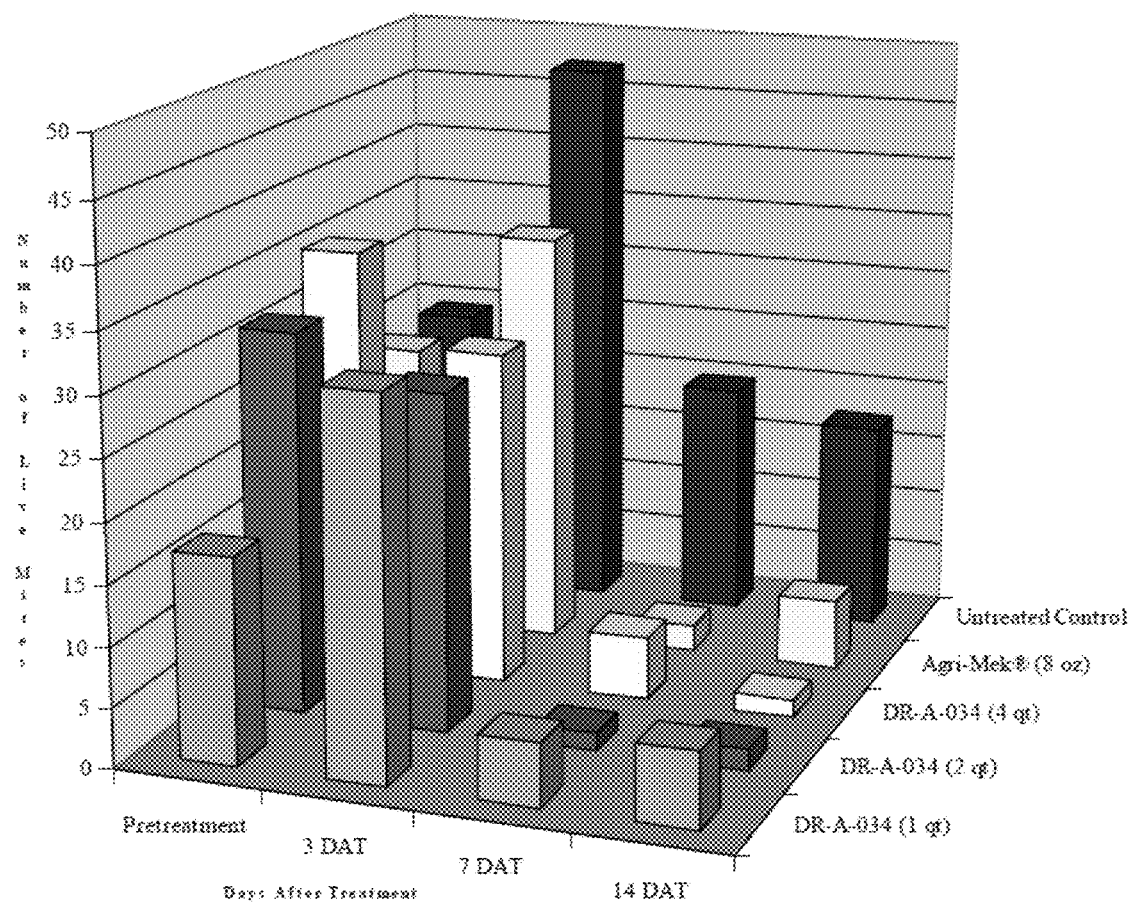
Figure 9:
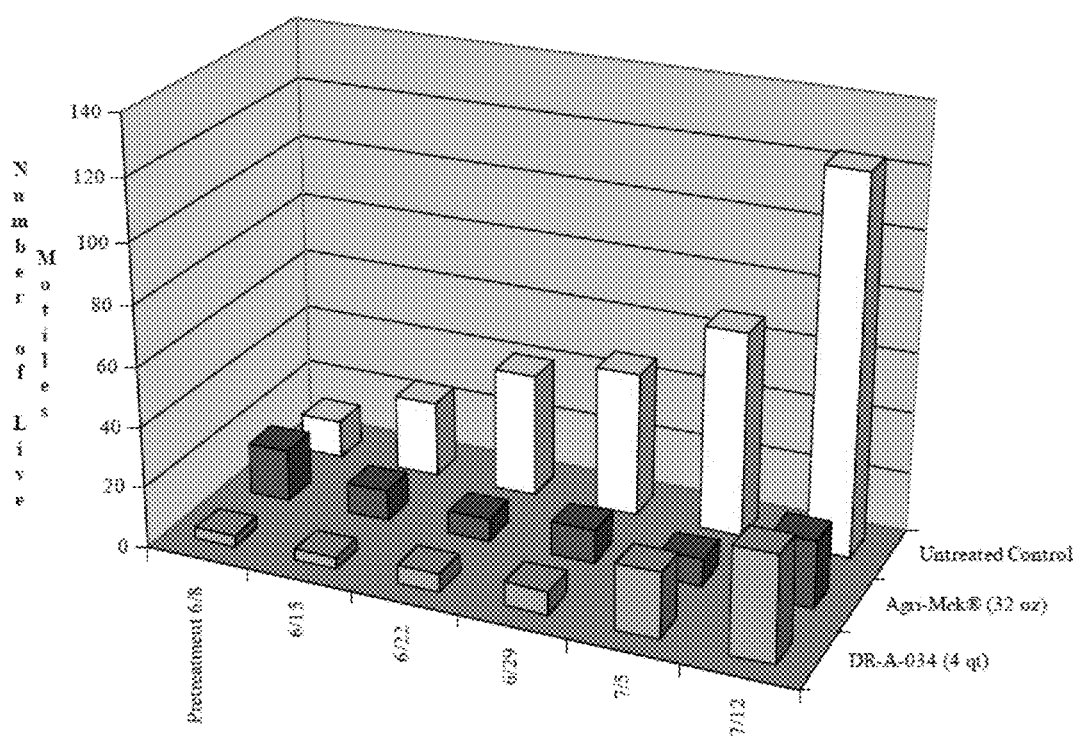
Figure 10:
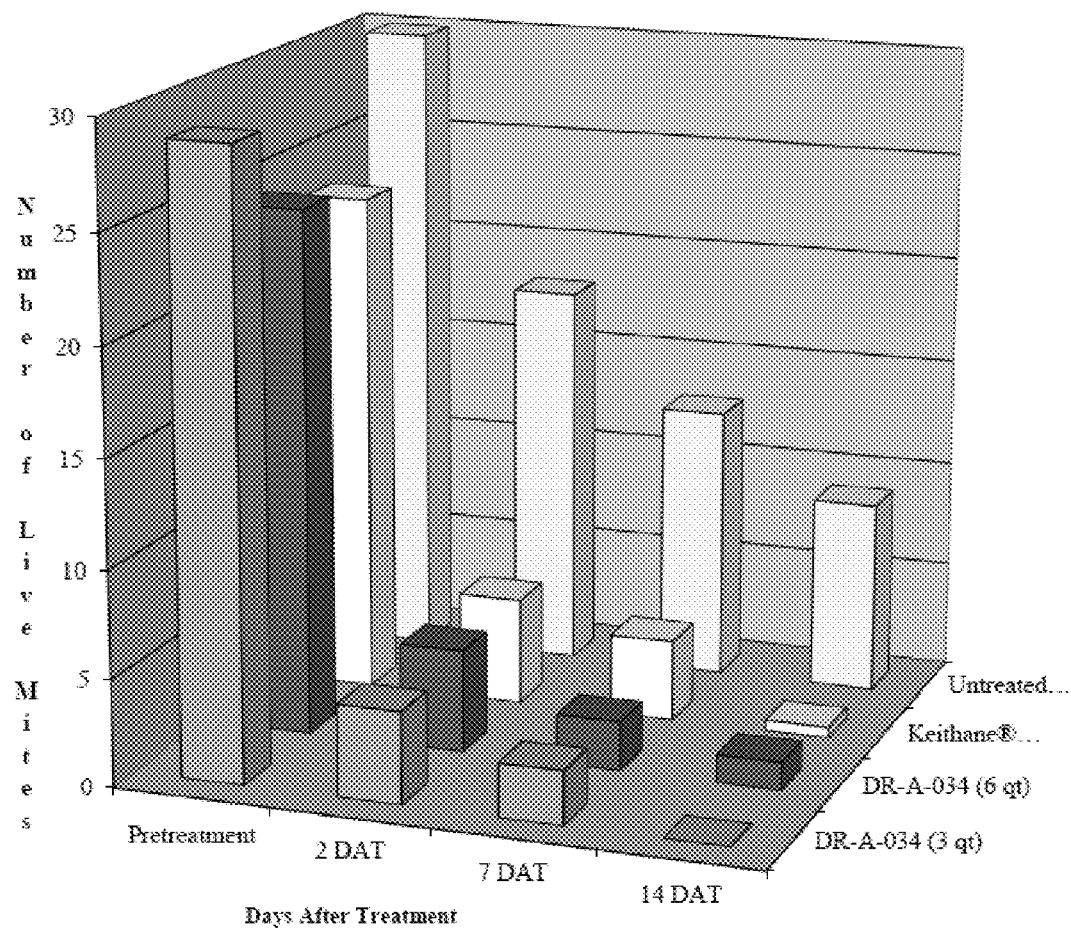
Figure 11:
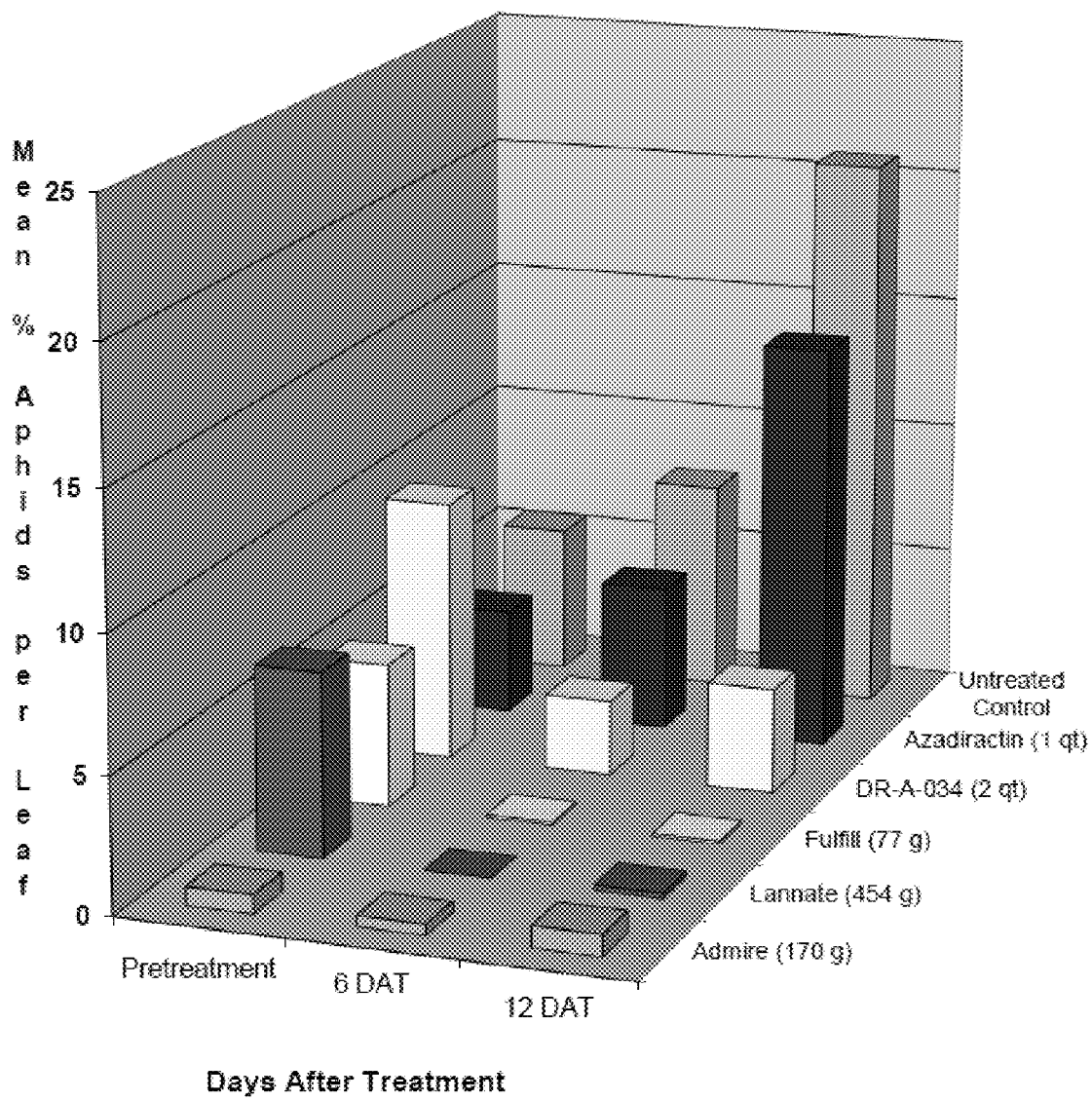

All patents, patent applications and literatures cited in this description are incorporated herein by reference in their entirety.

The inventors have surprisingly found that the pesticidal compositions containing rosemary oil and/or wintergreen oil have a broad spectrum of activity and are particularly effective against, but not limited to, insects having a cuticle or proteinaceous exoskeleton or the like. Furthermore, the composition according to the present invention, comprises additional natural or essential oils as additional components and is therefore particularly advantageous in terms of its relative non-toxicity.

The present invention provides very efficacious pesticides that, in a preferred aspect, may be designated as biopesticides in that they comprise a chemical substance of natural origin that can be synthesized. The preferred pesticidal composition of the present invention have a lethal effect on pest targets. Unlike the bulk of currently available pesticides on the market, the preferred pesticidal compositions have active ingredients that have been proven to be substantially non-toxic to man and domestic animals and which have minimal adverse effects on wildlife and the environment.

The pesticidal compositions of the present invention are advantageous in that they can typically control pests at average or lower than average dosage rates. Such pesticidal compositions are also advantageous in that they can provide extended protection to a locus. Further, such pesticidal compositions are also advantageous in that said pesticidal compositions control pests without introducing a notable amount of harm to the surrounding environment of which the provided pesticidal composition is being utilized.

The pesticidal compositions of the invention have pesticidal activity against one or more pests. However, it is understood that certain pesticidal compositions may be more effective on some pests than others, and may even be ineffective against some pests. However, that does not in any way detract from their value as pesticides since the present invention contemplates use as broad, general acting pesticides, while others have utility as specific or selective pesticides. The non-limiting Examples set forth below illustrate methods by which the broad-acting or selectivity of pesticidal activity may be readily ascertained by routine experimentation.

The pesticidal compositions of the present invention offer several advantages over currently used pesticides. First, the preferred essential oils used in the composition of the invention are naturally occurring compounds, and as such are relatively nontoxic to humans, domestic animals and wildlife.

Consequently, when used for treating plant pests, food crops can be treated using the composition up to and immediately before the harvesting period, a practice that generally is avoided when using conventional methods of pest control. The composition also can be used to control the growth of pest organisms on harvested crops. The harvested food can be used directly as food for animals or humans with little fear of (residual toxicity) or phytotoxicity. By using the subject compositions, the environmental and health hazards involved in pest control are minimized. Because of the versatility and broad spectrum of the present composition, when necessary, the composition can be used as a preventative on a repeated basis and, thus, can be integrated into integrated pest management (IPM) programs. The composition can be applied to skin or to objects such as clothing, fur, feathers, or hair that come into contact with skin when used to treat pests that infest animals. The essential oils, i.e., the active ingredients, of the pesticidal compositions of the present invention are believed to be biorational chemicals that may qualify for the US EPA Biopesticide Program.

Another advantage of the pesticidal compositions of the present invention is that they have not previously been used against microorganisms, and therefore, fungal and bacterial pathogens and other pest organisms have not acquired resistance to them. Disease resistance to chemicals other than the heavy metals occurs commonly in pests such as fungi and on rare occasions in bacterial plant disease pests. A new pesticide often becomes noticeably less effective against a particular disease after several growing seasons. As pesticides become more specific for diseases, the pests become resistant. This can be attributed to the singular mode of action of a particular pesticide, which disrupts only one genetically controlled process in the metabolism of the pest organism. The result is that resistant populations appear suddenly, either by selection of resistant individuals in a population or by a single gene mutation. Generally, the more specific the site and mode of a pesticidal action, the greater the likelihood for a pest organism to develop a tolerance to that chemical. A new composition will solve the disease resistance problem. To avoid developing future disease resistance in pests, different chemicals should be alternated for treatment with the methods of the invention.

Methods of using the pesticidal compositions of the present invention offer several advantages over existing methods of pest control. The formulations of the subject invention provide for effective control of (microorganisms) insects, mites, fungiand microorganisms In particular situations, such as where an insect damages a plant part or tissue and a secondary fungal disease develops, this aspect of the invention is particularly advantageous. The pesticidal compositions according to the invention have very good fungicidal properties and can be employed for controlling phytopathogenic fungi, such as, without limitation, plasmodiophoromycetes, oomycetes, chytridiomycetes, zygomycetes, ascomycetes, basidiomycetes, deuteromycetes, etc. Fungal phytopathogens particularly associated with crop plants and included within the scope of the present invention include, without limitation, the following: Miscellaneous Fungal Diseases (e.g., *Septoria tritici, Septoria nodorum*); *Gibberella* ear mold (e.g., e.g., *Gibberella zeae, G. saubinetti*); *Aspergillus* ear rot (e.g., *Aspergillus flavus, A. parasiticus*); *Diplodia* ear rot (e.g., *Diplodia maydis, D. macrospora*); *Fusarium* ear rot (e.g., *Fusarium moniliforme, F. monilif.* var. *subglutinans*); *Pythium* stalk rot (e.g., *Pythium aphanidermata*); Anthracnose stalk rot (e.g., *Colletotrichum graminicola, C. tucumanensis, Glomerella graminicola*); *Diplodia* stalk rot (e.g., *Diplodia maydis, D. zeae-maydis,* *Stenocarpella maydis, Macrodiplodia zeae, Sphaeria maydis, S. zeae, D. macrospora*); *Fusarium* stalk rot (e.g., *Fusarium moniliforme*); *Gibberella* stalk rot (e.g., *G. zeae, G. saubinetti*); Stewart's wilt & leaf blight (e.g., *Erwinia stewartii*); Northern corn leaf blight (e.g., *Exserohilum turcicum*); Southern corn leaf blight (e.g., *Bipolaris maydis*); Gray leaf spot (e.g., *Cercospora zeae-maydis, C. sorghi* var. *maydis*); Anthracnose leaf blight (e.g., *Colletotrichum graminicola*); Common rust (e.g., *Puccinia sorghi, P. maydis*); Southern rust (e.g., *Puccinia polysora, Dicaeoma polysorum*); Head smut (e.g., *Sphacelotheca reiliana*); Common smut (e.g., *Ustilago maydis*); Carbonum leaf spot (e.g., *Helminthosporium carbonum*); Eye spot (e.g., *Kabatiella zeae*); Sorghum downy mildew (e.g., *Peronosclerospora sorghi*); Brown stripe downy mildew (e.g., *Sclerophthora rayssiae*); Sugarcane downy mildew (e.g., *Peronosclerospora sacchari*); Phillipine downy mildew (e.g., *Peronoscler. Philippinensis*); Java downy mildew (e.g., *Peronosclerospora maydis*); Spontaneum downy mildew (e.g., *Peronosclerospora spantanea*); Rajasthan downy mildew (e.g., *Peronosclerospora heteropogoni*); Graminicola downy mildew (e.g., *Sclerospora graminicola*); Rusts (e.g., *Puccinia graminis* f.sp. *tritici, Puccinia recondita* f.sp. *tritici, Puccinia striiformis*); Smuts (e.g., *Tilletia tritici, Tilletia controversa, Tilletia indica, Ustilago tritici, Urocystis tritici*); Root rots, Foot rots and Blights (e.g., *Gaeumannomyces graminis, Pythium* spp., *Fusarium culmorum, Fusarium graminaerum, Fusarium avenaceum, Drechslere tritici-repentis, Rhizoctonia* spp., *Colletotrichum graminicola, Helminthosporium* spp., *Microdochium nivale, Pseudocercosporella herpotrichoides*); Mildews (e.g., *Erysiphe graminis* f.sp. *tritici, Sclerophthora macrospora*), and the like.

The long term control of pests results in plants with an improved quality and yields of produce by host plants as compared with untreated plants. The low concentration and single dose of anti-pest agents decreases the likelihood of damage to the plant and/or its crop, and decreases the likelihood of adverse side effects to workers applying the pesticide, or to animals, fish or fowl which ingest the tissues or parts of treated plants. The methods of use of the pesticidal compositions of the invention will depend at least in part upon the pest to be treated and its feeding habits, as well as breeding and nesting habits. While very minor dosage rates of the novel compositions will have an adverse effect on pests, adequate control usually involves the application of a sufficient amount to either eliminate pests entirely or significantly deter their growth and/or rate of proliferation. Dosage rates required to accomplish these effects, of course, vary depending on the target pest, size, and maturity, i.e., stage of growth. More mature pests may be more resistant to pesticides and require higher dosage rates for a comparable level of control. Dose response experiments using different dilutions (for example, about 1:1000, 1:100, 1:10 and 1:3) of the pesticidal compositions of the present invention on target organisms and on plants are performed to determine the optimal concentration of the active essential oil compound(s) that show(s) pesticidal activity without phytotoxicity or dermal sensitivity. For instance, when the pesticidal composition of the present invention is utilized for agricultural purposes, an amount from about 0.1 to 2,000 (SMB has a question mark by this) g/ha of the active ingredients is employed onto the soil, plants, or directly onto the harmful pests, preferably as an emulsifiable concentrate or emulsion usually at a rate from 1 to 2000 ppm.

In preferred embodiment, a pesticidal composition of the present invention useful for treating (e.g., preventing, controlling, impeding, and the like) infectious or pathogenic bacterial, viral, microbial, and other diseases causing pests is provided which includes applying an effective amount of the pesticidal composition to a locus in need thereof for controlling, treating, managing, preventing, or the like, the spread of diseases caused by germs, bacteria, or viruses such as *Escherichia coli, salmonella*, staphylococci, streptococci, influenza, pneumonia, various blood and urine bacterial pathogens, and the like. The present invention further encompasses treatment of the following: gram-positive cocci that cause staphylococcal infections such as pneumonia, bacteremia, osteomyelitis, enterocolitis, and the like; streptococci that cause infections such as hemolytic, viridans, enterococci, lactic, and the like; pneumococci that cause infections such as pneumonia, sinusitis, otitis, Meningitis, and the like; gram-negative cocci such as meningococcus, gonococcus, and the like; gram-positive bacilli that cause infections such as erysipelothricosis, listeriosis, anthrax, nocardiosis, and the like; gram-negative bacilli that cause infections such as enterobacteriaceac *salmonella*, shigellosis, hemophilus, tularemia, plaque, melioidosis, bartonellosis, *campylobacter*, and non-cholera *vibrio*, and the like; anaerobic bacilli that cause infections such as *clostridium botulinum, clostridium tetany*, clostridia of gas gangrene bacteroides, mixed anaerobic, actinomycosis, and the like; mycobacteria that cause infections such as tuberculosis and leprosy, and the like; and spirochetes that cause diseases such as leptospirosis, lyme disease, and endemic treponematoses. Further, the present invention, the pesticidal compositions may be useful for treating surfaces containing infectious human immunodeficiency virus (HIV), influenza, A, B, and C, parainfluenza viruses 1-4, rhonoviruses (common cold), mumps virus, adenoviruses, reoviruses, and epstein-Barr virus, infants and adult syncytial virus, primary atypical pneumonia, polioviruses, coxsackieviruses, echoviruses and high numbered viruses, epidemic gastroenteritis viruses, rubeola virus, rubella virus, varicella-zoster virus, herpes simplex, human herpes virus type 6, human parvovirus B19, cytomegalovirus, hepatitis viruses types A, B, C, D, human Papillomavirus, molluscum contagiosum virus, arboviruses, togaviruses, alphaviruses, flaviviruses, bunyaviruses, orbivirus, rabies virus, herpesvirus simiae, arenaviruses, filoviruses, and the like.

In a preferred embodiment, the present invention provides a pesticidal composition comprising rosemary oil and wintergreen oil in admixture with mineral oil, lecithin and water. In this embodiment, rosemary oil is present in an amount of about 5-10%, wintergreen oil is present in an amount of about 20-45%, and mineral oil present in an amount of about 20-45%.

In another embodiment, the present invention provides a pesticidal composition comprising rosemary oil and wintergreen oil in admixture with mineral oil. In this embodiment, rosemary oil is present in an amount of about 5-20%, wintergreen oil is present in an amount of about 20-80%, and mineral oil is present in an amount of about 5-45%.

In another embodiment, the present invention provides a pesticidal composition comprising rosemary oil and wintergreen oil in admixture with thyme oil and mineral oil.

In another embodiment, the present invention provides a pesticidal composition comprising rosemary oil and wintergreen oil in admixture with 2-phenethyl propionate and mineral oil.

In another embodiment, the present invention provides a pesticidal composition comprising rosemary oil and wintergreen oil in admixture with 2-phenethyl propionate, safflower oil and mineral oil.

In another embodiment, the present invention provides a pesticidal composition comprising rosemary oil and wintergreen oil with a suitable carrier and optionally with a suitable surface active agent, with and without one or more additional essential oil compounds and derivatives thereof, natural or synthetic, including racemic mixtures, enantiomers, diastereomers, hydrates, salts, solvates and metabolites, etc. Additional essential oils that may be included in the pesticidal composition of the present invention include, without limitation, members selected from the group consisting of α- or β-pinene; α-campholenic aldehyde; α-citronellol; α-isoamyl-cinnamic (e.g., amyl cinnamic aldehyde); α-pinene oxide; α-cinnamic terpinene; α-terpineol (e.g., methods. 1-methyl-4-isopropyl-1-cyclohexen-8-ol); λ-terpinene; achillea; aldehyde C16 (pure); alpha-phellandrene; amyl cinnamic aldehyde; amyl salicylate; anethole; anise; aniseed; anisic aldehyde; basil; bay; benzyl acetate; benzyl alcohol; bergamot (e.g., *Monardia fistulosa, Monarda didyma, Citrus bergamia, Monarda punctata*); bitter orange peel; black pepper; borneol; calamus; camphor; cananga oil (e.g., java); cardamom; carnation (e.g., *dianthus caryophyllus*); carvacrol; carveol; cassia; castor; cedar (e.g., hinoki); cedarwood; chamomile; cineole; cinnamaldehyde; cinnamic alcohol; cinnamon; cis-pinane; citral (e.g., 3,7-dimethyl-2,6-octadienal); citronella; citronellal; citronellol dextro (e.g., 3-7-dimethyl-6-octen-1-ol); citronellol; citronellyl acetate; citronellyl nitrile; *citrus* unshiu; clary sage; clove (e.g., eugenia caryophyllus); clove bud; coriander; corn; cotton seed; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin (e.g., 3-ethoxy-4-hydrobenzaldehyde); eucalyptol (e.g., cineole); *eucalyptus citriodora; eucalyptus globulus; eucalyptus*; eugenol (e.g., 2-methoxy-4-allyl phenol); evening primrose; fenchol; fennel; ferniol.tm.; fish; florazon (e.g., 4-ethyl-α,α-dimethyl-benzenepropanal); galaxolide; geraniol (e.g., 2-trans-3,7-dimethyl-2,6-octadien-8-ol); geraniol; geranium; geranyl acetate; geranyl nitrile; ginger; grapefruit; guaiacol; guaiacwood; gurjun balsam; heliotropin; herbanate (e.g., 3-(1-methyl-ethyl)bicyclo(2,2,1)hept-5-ene-2-carboxylic acid ethyl ester); hiba; hydroxycitronellal; i-carvone; i-methyl acetate; ionone; isobutyl quinoleine (e.g., 6-secondary butyl quinoline); isobornyl acetate; isobornyl methyl-ether; isoeugenol; isolongifolene; jasmine; jojoba; juniper berry; lavender; lavandin; lemon grass; lemon; lime; limonene; linallol oxide; linallol; linalool; linalyl acetate; linseed; litsea cubeba; l-methyl acetate; longifolene; mandarin; *mentha*; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; mineral; mint; musk ambrette; musk ketone; musk xylol; mustard (also known as allylisothio-cyanate); myrcene; nerol; neryl acetate; nonyl aldehyde; nutmeg (e.g., *myristica fragrans*); orange (e.g., *citrus aurantium dulcis*); orris (e.g., *iris florentina*) root; para-cymene; para-hydroxy phenyl butanone crystals (e.g., 4-(4-hydroxyphenyl)-2-butanone); passion palmarosa oil (e.g., *cymbopogon martini*); patchouli (e.g., *pogostemon cablin*); p-cymene; pennyroyal oil; pepper; peppermint (e.g., *mentha piperita*); perillaldehyde; petitgrain (e.g., *citrus aurantium amara*); phenyl ethyl alcohol; phenyl ethyl propionate; phenyl ethyl-2-methylbutyrate; pimento berry; pimento leaf; pinane hydroperoxide; pinanol; pine ester; pine needle; pine; pinene; piperonal; piperonyl acetate; piperonyl alcohol; plinol; plinyl acetate; pseudo ionone;

rhodinol; rhodinyl acetate; rosalin; rose; rosemary (e.g., *rosmarinus officinalis*); ryu; sage; sandalwood (e.g., *santalum album*); sandenol; sassafras; sesame; soybean; spearmint; spice; spike lavender; spirantol; starflower; tangerine; tea seed; tea tree; terpenoid; terpineol; terpinolene; terpinyl acetate; tert-butylcyclohexyl acetate; tetrahydrolinalool; tetrahydrolinalyl acetate; tetrahydromyrcenol; thulasi; thyme; thymol; tomato; trans-2-hexenol; trans-anethole and metabolites thereof; turmeric; turpentine; vanillin (e.g., 4-hydroxy-3-methoxy benzaldehyde); vetiver; vitalizair; white cedar; white grapefruit; (wintergreen) and the like.

In a further example embodiment, suitable essential oils or their constituents may include, but are not limited to, members selected from the group consisting of aldehyde C16 (pure), alpha-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, dimethyl salicylate, eucalyptol (cineole), eugenol, iso-eugenol, galaxolide, geraniol, guaiacol, ionone, d-limonene, menthol, methyl anthranilate, methyl ionone, methyl salicylate, alpha-phellandrene, pennyroyal oil, perillaldehyde, 1- or 2 phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil (white and red), thymol, trans-anethole, vanillin, ethyl vanillin, and the like.

In an example embodiment, each plant essential oil or derivative thereof, which may be extracted from natural sources or synthetically made, generally contains as a major constituent an acyclic monoterpene alcohol or aldehyde, a benzenoid aromatic compound containing at least one oxygenated substituent or side chain, or a monocarbocyclic terpene generally having a six membered ring bearing one or more oxygenated substituents.

As plant essential oil compounds are known and used for other uses, they may be prepared by a skilled artisan by employing known methods. For example, the synthetic form of wintergreen oil (methyl salicylate) may also be used in the embodiment.

It will be appreciated by the skilled artisan that the pesticidal compositions of the present invention unexpectedly exhibit excellent pesticidal activities using two or more U.S. Food and Drug Administration approved plant essential oils, in lieu of conventional pesticides which are not safe for use in households and other sensitive areas, or in lieu of pesticidal compositions containing individual plant essential oils. It will also be appreciated by the skilled artisan that the pesticidal compositions of the present invention provide affordable pesticidal formulations that are aesthetically acceptable. It will also be appreciated by the skilled artisan that the pesticidal compositions of the present invention unexpectedly exhibit excellent pesticidal activities, specifically knockdown and mortality, using water-based emulsions in both pressurized (e.g. an aerosol) and non-pressurized systems in lieu of oil based solvent systems.

Without wishing to be bound by the following theories, it is believed that the plant essential oils attack a pest's nervous system or may act as Phase I and/or Phase II drug metabolizing enzyme inhibitors. Alternatively, pesticidal compositions of the present invention may act via an alternative mode of action, as agonists or antagonists against the nerve receptor systems that are distinct to invertebrates, e.g., the octopamine receptor system. As octopamine agonists, the pesticidal compositions of the present invention act by binding to a receptor that activates adenylate cyclase which, in turn, produces secondary messenger cyclic AMP. The cyclic AMP acts by binding to a cyclic AMP receptor generating hormonal-type activity. Pesticidal compositions of the present invention are highly active and are believed to have activities unexpectedly greater than octopamine. The term "octopamine agonist" is meant to indicate a compound that mimics at least some of the effects of octopamine by interaction with the octopamine receptor. For example, an octopamine agonist, like endogenous octopamine, may affect many areas of insect physiology, including carbohydrate metabolism, lipid mobilization, hematocyte function, heart rate, peripheral muscle tension and excitability, and behavior. Thus, overactivation of the octopamine system in certain pests by an octopamine agonist may lead to behavioral and physiological abnormalities that have peststatic and pesticidal consequences. As octopamine agonists, the pesticidal compositions of the present invention act as highly selective pest control agents since vertebrate species—as opposed to invertebrate, e.g., insect, species—lack octopamine receptors. As a result, any octopamine-receptor containing pest is treatable or controllable by the pesticidal compositions of the present invention. These pests include all invertebrate pests, including, but not limited to, round worms (e.g., hookworm, trichina, ascaris); flatworms (e.g., liver flukes and tapeworms); jointed worms (e.g., leeches); molluscs (e.g., parasitic snails); and arthropods (insects, spiders, centipedes, millipedes, crustaceans (e.g., barnacles)). In particular, included among the arthropods are ticks; mites (both plant and animal); lepidoptera (butterflies and moths and their larvae); hemiptera (bugs); homoptera (aphids, scales); and coleoptera (beetles). Also included are spiders; anoplura (lice); diptera (flies and mosquitoes); trichoptera; orthoptera (e.g., roaches); odonta; thysanura (e.g., silverfish); collembola (e.g., fleas); dermaptera (earwigs); isoptera (termites); ephemerids (mayflies); plecoptera; mallophaga (biting lice); thysanoptera; and siphonaptera (fleas); dictyoptera (roaches); psocoptera (e.g., booklice); and certain hymenoptera (e.g., those whose larva feed on leaves). In another embodiment of the invention, there is provided a method for controlling pests by treating said pests with an octopamine agonist of the invention in an amount effective to provide pest control, by either pesticidal or peststatic activity.

In one aspect, the pesticidal compositions may use surfactants as part of the delivery or carrier system. The presence of nonionic, cationic or anionic surfactants, such as, sodium lauryl sulfate, nonyl phenoxypolyoxyethylene and hydrogenated tallow dimethyl benzyl ammonium chloride, can be used as adjuvants. Adjuvants are believed to confer the broad spectrum pesticidal activity on the composition by acting as a wetting, dispersing and/or emulsifying agent that facilitates or aids in the spreading of the active rosemary and wintergreen oils across an insect or larva, providing for a more uniform and rapid penetration of the oils through the exoskeleton (if present), thus permitting the oils to exert their pesticidal activity on the internal organs and/or nervous system of the insect or larva. Non-limiting examples of anionic surfactants such as salts of fatty acids, alkyl sulphates, alkyl ether sulphonates and alkyl aryl sulphonates. Other examples of preferred surfactants include sodium dodecyl benzenesulfonic acid, alcohol ethoxylate, olefin sulfonate, and modified phthalic glycerol alkyd resins such as Latron B1956.

In another aspect, the plant essential oils of the present invention may act as solvents against the waxy cuticle protecting invertebrate pests, thereby penetrating the cuticle and causing fast knockdown and mortality. The plant essential oils may penetrate the cuticle and contact the nerve endings in the invertebrate pest's trachea, and cause neurotoxic activity.

In any event, the net effect of the toxicity and action of the inventive composition disclosed herein is heretofore unknown and unexpected.

Use of pesticidal compositions of the present invention generally results in fast knockdown and 100% mortality on contact. As such, they are advantageously employed as pesticidal agents in uses such as, without limitation, households, lawn and garden applications, agriculture, organic farming, greenhouse/nursery applications, stored product applications, professional pest control, pet bedding, foliage application, underwater or submerged application, solid treatment, soil incorporation application, seedling box treatment, stalk injection and planting treatment, ornamentals, termites, mosquitoes, fire ants, head lice, dust mites, etc. Use of the pesticidal compositions of the present invention generally provides repellency to pests, and as such are advantageously employed as plant protectants.

With respect to soil, the pesticidal compositions resist weathering which includes wash-off caused by rain, decomposition by ultra-violet light, oxidation, or hydrolysis in the presence of moisture or, at least such decomposition, oxidation and hydrolysis as would materially decrease the desirable pesticidal characteristic of the pesticidal compositions or impart undesirable characteristics to the pesticidal compositions. The pesticidal compositions are so chemically inert that they are compatible with substantially any other constituents of pest control, and they may be used in the soil, upon the seeds, or the roots of plants without injuring either the seeds or roots of plants. They may also be used in combination with other pesticidally active compounds.

The term "carrier" as used herein means an inert or fluid material, which may be inorganic or organic and of synthetic or natural origin, with which the active compound is mixed or formulated to facilitate its application to the container or carton or other object to be treated, or its storage, transport and/or handling. The pesticidal compositions of the instant invention also typically comprise an inert carrier, in an amount in which the inert carrier can assist the instant active ingredient to be carried through a process or method of controlling pests. As such an amount of the inert carrier, the inventive pesticidal compositions preferably comprise the inert carrier in an amount of from about 5-99.9%, provided that such a carrier is a solid, liquid or gas carrier, or a combination thereof. In such a case, examples of the solid carriers that may be in the pesticidal compositions of the instant invention include clays such as kaolin, diatomaceous earth, bentonite, fubasami clay and terra alba, synthetic hydrated silicon oxides, talc, ceramics, other inorganic minerals which are useful in producing formulated compositions such as sericite, quartz, sulfur, active carbons and calcium carbonate, chemical fertilizers such as ammonium sulfate, ammonium phosphate, ammonium nitrate, urea and ammonium chloride, and the like, as well as powders thereof, granules thereof, and a mixture thereof; examples of the liquid carriers that may be in the pesticidal compositions of the instant invention include water, alcohols such as methanol and ethanol, aromatic hydrocarbons such as toluene, xylene, ethylbenzene and alkyl naphthalenes, non-aromatic hydrocarbons such as hexane, cyclohexane, kerosene, isoparoffinic and normal paroffinic solvents and light oils, esters such as ethyl acetate and butyl acetate, nitrites such as acetonitrile and isobutylonitrile, ethers such as diisopropyl ether and dioxane, amides such as N,N-dimethylformamide and N,N-dimethylacetamide, halogenated hydrocarbons such as dichloromethane, trichloroethane and carbon tetrachloride, dimethylsulfoxide, botanical oils such as soy oil and cotton seed oil, and the like, and a mixture thereof; and examples of the gas carriers that may be in the aerosol form of pesticidal compositions of the instant invention include propellants such as butane gas, propane gas, liquid petroleum gas, dimethyl ether, carbon dioxide, and the like, and a mixture thereof.

In general, any of the materials customarily employed in formulating pesticides, (insecticides, miticides, herbicides, fungicides, etc.) are suitable. The inventive pesticidal compositions of the present invention may be employed alone or in the form of mixtures with such solid and/or liquid dispersible carrier vehicles and/or other known compatible active agents such as other insecticides, acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The pesticidal compositions of the present invention can be formulated or mixed with, if desired, conventional inert pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc. In addition, mineral oil and the essential oils disclosed herein (e.g., safflower oil, benzyl alcohol, citronellal, d-limonene, soybean oil, sesame oil, etc.) may also serve as diluents or carriers in the pesticidal compositions of the present invention.

Formulations containing the pesticidal compositions of the present invention may be prepared in any known manner, for instance by extending the pesticidal compositions with conventional liquid carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the pesticidal compositions of the present invention. Non-ionic, anionic, amphoteric, or cationic dispersing and emulsifying agents may be employed, for example, the condensation products of alkylene oxides with phenol and organic acids, alkyl aryl sulfonates, complex ether alcohols, quarternary ammonium compounds, and the like.

Liquid concentrates may be prepared by dissolving a composition of the present invention with a solvent and dispersing the pesticidal compositions of the present inventions in water with suitable surface active emulsifying and dispersing agents. Examples of conventional carrier vehicles for this purpose include, but are not limited to, aerosol organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and water.

Surface-active agents, i.e., conventional carrier vehicle assistants, that may be employed with the present invention include, without limitation, emulsifying agents, such as nonionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers. In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which act as carriers for the pesticide. These finely divided solids preferably have an average particle size of less than about 5 microns. A typical dust formulation useful for controlling insects contains 5 parts of pesticidal composition and 95 parts of diatomaceous earth or vermiculite. Granules may comprise porous or nonporous particles. The granule particles are relatively large, a diameter of about 400-2500 microns typically. The particles are either impregnated or coated with the inventive pesticidal compositions from solution. Granules generally contain 0.05-25%, preferably 0.5-15%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, peanuts, apple pomace, recycled paper, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrates.

Further, the pesticidal compositions of the instant invention may additionally contain a coloring agent, a formulation auxiliary, or a combination thereof. As such, examples of such coloring agents that may be utilized in the pesticidal compositions of the instant invention include inorganic pigments such as metal oxides, titanium oxides and Prussian blue, organic dyes such as alizarine dyes, azo dyes and metallic phthalocyanine dyes, iron, manganese, boron, copper, cobalt, molybdenum, zinc and salts thereof, and the like, or a mixture thereof; and examples of such formulation auxiliaries that may be utilized in the pesticidal compositions of the instant invention include attaching and/or dispersing agents, surfactants, stabilizers, and the like, or a mixture thereof.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

In commercial applications, the present invention encompasses carrier composition mixtures in which the pesticidal compositions are present in an amount substantially between about 0.01-100% by weight, and preferably 0.5-90% by weight, of the mixture, whereas carrier composition mixtures suitable for direct application or field application generally contemplate those in which the active compound is present in an amount substantially between about 0.0001-10%, preferably 0.01-2%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-100%, and preferably 0.01-95%, by weight of the mixture.

The pesticidal compositions can also be used in accordance with so-called ultra-low-volume process, i.e. by applying such compounds or by applying a liquid composition containing the same, via very effective atomizing equipment, in finely divided form, e.g. average particle diameter of from 50-100 microns, or even less, i.e. mist form, for example by airplane crop spraying techniques. In this process it is possible to use highly concentrated liquid compositions with said liquid carrier vehicles containing from about 20 to 95% by weight of the pesticidal compositions or even the 100% active substances alone, e.g. about 20-100% by weight of the pesticidal compositions. The concentration in the liquid concentrate will usually vary from about 10 to 95 percent by weight. Furthermore, the present invention encompasses methods for killing, combating or controlling invertebrate pests, which comprises applying to at least one of correspondingly (a) such invertebrate pests and (b) the corresponding habitat thereof, i.e. the locus to be protected, e.g. to the household, a correspondingly combative, a pesticidally effective amount, or toxic amount of the particular pesticidal compositions of the invention alone or together with a carrier as noted above. The instant formulations or compositions may be applied in any suitable usual manner, for instance by spraying, atomizing, vaporizing, scattering, dusting, watering, squirting, sprinkling, pouring, fumigating, and the like. The method for controlling invertebrate pests such as cockroaches and ants comprises applying the inventive composition, ordinarily in a formulation of one of the aforementioned types, to a locus or area to be protected from the cockroaches and/or ants, such as the household. The compound, of course, is applied in an amount sufficient to effect the desired action. This dosage is dependent upon many factors, including the targeted pest, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected, i.e., the dosage with which the pest comes in contact-is of the order of about 0.001 to about 5.0% based on the total weight of the formulation, though under some circumstances the effective concentration will be as little as 0.0001% or as much as 20%, on the same basis.

The pesticidal compositions and methods of the present invention are effective in the control of different species of invertebrate pests and it will be understood that the pests exemplified and evaluated in the working Examples herein is representative of such a wider variety. By way of example, but not limitation, the pesticidal compositions of the present invention are also useful for control of pests such as fleas, mosquitoes, bees such as yellow jackets and wasps, cockroaches including the American and German cockroach, termites, houseflies and silverleaf whiteflies (*Bemisia argentifolii*), leaf hoppers such as the grape or potato leafhoppers (Cicidellidae), cabbage looper (Lepidoptera), ants such as the pharaoh ant, argentine ant, carpenter ant and fire ant, stink or lygus bugs, leafminers (*Liriomyza trifollii*), western flower thrips (*Frankliniella occidentalis*) and sucking or chewing insects such as thrips and aphids such as melon aphids (*Aphis gossypii*), black bean aphids (*Aphis fabae*); arachnids such as spiders, ticks and plant mites, including two-spotted spider mites (*Tetronmychua urticae*), McDaniel mites, Pacific mites and European mites; gastropods such as slugs and snails; fungi such as powdery mildew including *cladosporium*, strawberry powdery mildew, rusts, botrytis, ergots, blight, downy mildew, eutypa, leaf spot, smut, Chytridimycota, Zygomycota, Asomycota, ringworm, *rhizopus*, *rhizoctonia*, *pythium* and *erwinia*; nematodes; and bacteria. Further targeted pests controlled by the pesticidal composition of the present invention are, for example, the pillbugs and Isopoda (sowbugs) such as *Oniscus asellus*, *Armadillidium vulgare* (Latreille pillbug) and *Porcellio scarber, Pieris rapae crucivora* (common cabbageworm), *Spodoptera litura* (tobaccocutworm), *Thrips palmi* (melon *thrips*), *Empoasca onukii* (tea green leafhopper), *Phyllonorycter ringoniella* (appleleafminer), *Lissorhoptrus oryzophilus* (rice water weevil), *Popillia japonica* (Japanese beetle), *Phyllotreta* (striped flea beetle), *Tetranychus kanzawai* (Kanzawa spidermite), *Polyphagotarsonemus latus* (broad mite); Diplopoda such as *Blanilus guttulatus* (millepede); Chilopoda such as *Geophilus carpophagus, Scutigera* spp., *Scolopendra subspini* and *Thereunema* spp.; Symphyla such as *Scutigerella immaculata*; Thysanura (bristletails) such as *Ctenolepisma villosa* (oriental silverfish) and *Lepisma saccharina* (silverfish); Psocoptera such as *Trogium pulsatorium* (larger pale booklice); Collembola (snowfleas) such as *Onichiurus armatus*; Isoptera (termites) such as Mastotermitidae, Termopsidae (e.g. *Zootermopsis, Archotermopsis, Hodotermopsis, Porotemes*), Kalotermitidae (e.g. *Kalotermes, Neotermes, Cryptotermes, Incisitermes, Glyptotermes*), Hodotermitidae (e.g. *Hodotermes, Microhodotermes, Anacanthotermes*), Rhinotermitidae (e.g. *Reticulitermes, Heterotermes, Coptotermes, Schedolinotermes*), Serritermitidae and Termitidae (e.g. *Anitermes, Drepanotermes, Hopitalitermes, Trinervitermes, Macrotermes, Odontotermes, Microtermes, Nasutitermes, Pericapritermes, Anoplotermes*); Dictyoptera (cockroaches) such as *Blatta orientalis* (oriental cockroach), *Periplaneta americana* (American cockroach), *Periplaneta fuliginosa* (smokybrown cockroach), *Leucophaea maderae* and *Blattella germanica* (German cockroach); Orthoptera such as *Gryllotapa* spp. (mole cricket), *Acheta domesticus, Teleogryllus emma* (field cricket), *Locusta migratoria* (asiatic locust/oriental migratory locust), *Melanoplus differentialis* and *Schistocera gregaria*; Dermaptera (earwigs) such as *Labidura riparia* and *Forficula auricularia*; Anoplura such as *Phthirus pubis, Pediculus humanus, Haematopinus sulus, Linognathus* spp. and *Solenopotes* spp.; Mallophaga such as *Trichodectes* spp., *Tromenopon* spp., *Bovicola* spp. and *Felicola* spp.; Thysanoptera (*thrips*) such as *Frankiniella intonsa* (flower *thrips*), onion *thrips, Thrips tabaci* (cotton seedling *thrips*) and *Thrips palmi*; Heteroptera such as *Nezara* spp., *Eurygaster* spp., *Dysdercus intermedius, Cimex lectularis, Triatoma* spp., *Rhodnius prolixus, Nezara antennata* (green stink bug) and *Cletus puncttiger*; Homoptera such as *Aleurocanthus spiniferus* (*citrus* spiny whitefly), *Bemisia tabaci* (sweetpotato whitefly), *Trialeurodes vaporariorum* (greenhouse whitefly), cotton asphid, *Aphis gossypii* (melon aphid), *Brevicoryne brassicae* (cabbage asphid), *Cryptomyzus ribis, Aphis fabae, Macrosiphum euphorbiae* (potato aphid), *Myzus persicae* (green peach aphid), *Phorodon humuli, Empoasca* spp., *Nephootettix cincticeps* (green rice leafhopper), *Lecanium corni* (brown scale), *Saissetia oleae* (black scale), *Laodelphax striatellus* (small brown plant hopper), *Nilaparvata lugens* (brown rice planthopper), *Aonidiella aurantii* (red scale), *Aspidiotus hederae* (ivy scale), *Pseudococcus* spp., *Psylla* spp. and *Phylloxera vastrix*; Lepidoptera such as *Pectinophora gossypiella* (pink bollworm), *Lithocolletis blancardella, Plutella xyloste* (diamondback moth), *Malacosoma neustria* (tent catapillar), *Euproctis subflava* (oriental tussock moth), *Lymantria dispar* (gypsy moth), *Bucculatrix pyrivorella* (pear leafminer), *Phyllocnistis citrella* (*citrus* leafminer), *Agrotis* spp., *Euxoa* spp., *Earias insulana, Heliothis* spp., *Spodoptera exigua* (beet armyworm), *Spodoptera litura* (common cutworm), *Spodoptera* spp., *Mamestra brassicae* (cabbage armyworm), *Trichoplusia ni, Carpocapsa pomonella, Pieris* spp., *Chilo* spp., *Pyrausta nubilalis, Ephestia kuehniella* (Mediterranean flour moth), *Galleria mellonella* (greater wax moth), *Tineola bisselliella* (webbing clothes moth), *Tenea translucens*, oriental tea tortrix (*Homona magnanima*) and *Totrix viridana*; Coleoptera (beetles) such as *Anobium punctatum, Rhizopertha dominica* (lesser grain borer), *Acanthoscelides obectus* (bean weevil), *Agelastica alni, Leptinotarsa decemlineata, Phaedon cochleariae, Diabrotica* spp., *Psylliodes angusticollis* (solanum flea beetle), *Phyllotreta striolata* (striped flea beetle), *Epilachna* spp., *Atomaria* spp., *Oryzaephilus surinamensis* (sawtoothed grain beetle), *Anthonomus* spp., *sitophilus* spp., *Otriorhynchus sulcatus* (black vine weevil), *Cosmopolites sordidus* (banana weevil borer), *Ceuthorhyncidius albosuturalis, Hypera postica* (alfalfa weevil), *Dermestes* spp., *Trogoderma* spp., *Attagenus unicolor* (black carpet beetle), *Lyctus* spp., *Meligethes aeneus, Ptinus* spp., *Gibbium psylloides, Tribolium* spp., *Tenebrio molitor* (yellow mealworm), *Agriotes* spp., *Melolontha mololontha*, Scolytidae (e.g. *Xyleborus* and *Scolytoplatypus*), Cerambycidae (e.g. *Monochamus, Hylotrupes, Hesperophanus, Chlorophorus, Palaeocallidium, Semanotus, Purpuricenus, Stromatium*), Platypodidae (e.g. *Crossotarsus, Platypus*), Bostrychidae (e.g. *Dinoderus, Bostrychus, Sinoderus*), Anobiidae (e.g. *Ernobius, Anobium, Xyletinus, Xestobium, Ptilinus, Nicobium, Ptilneurus*) and Buprestidae; Hymenoptera such as *Diprion* spp., *Hoplocampa* spp., *Lasius* spp., *Formica japonica, Vespa* spp., and Siricidae (e.g. Urocerus, Sirex); Diptera such as *Aedes* spp., *Anopheles* spp., *Culex* spp., *Drosophila melanogaster, Musca domestica* (housefly), *Fannia* spp., *Calliphora* spp., *Lucilia* spp., *Chrysomya* spp., *Cuterebra* spp., *Gastrophilus* spp., *Stomoxys* spp., *Oestrus* spp., *Hypoderma* spp., *Tabanus* spp., *Bibio hortulanus, Pegomyia hyoscyami, Ceratitus capitata, Dacus dorsalis* (oriental fruit fly), *Tipula paludosa, Simulium* spp., *Eusimulium* spp., *Phlebotomus* spp., *Culicoides* spp., *Chrysops* spp., *Haematopota* spp., *Braula* spp., *Morellia* spp., *Glossina* spp., *Wohlfahrtia* spp., *Sarcophaga* spp., *Lipoptena* spp., *Melophagus* spp. and *Muscina* spp.; Siphonaptera such as *Xenopsylla cheopis, Ceratophyllus* spp., *Pulex* spp. (human flea) and *Ctenocephalides* spp. (cat flea/dog flea); Arachnida such as *Scorpio maurus, Latrodectus mactans* and *Chiracanthium* spp.; mites such as *Otodectus* spp., *Acarus siro* (grain mite), *Argas* spp., *Ornithodoros* spp., *Ornithonyssus* spp., *Dermanyssus* spp., *Eriophyes* spp., *Chelacaropsis moorei*, *Dermatophagoides* spp., *Psoroptes equi*, *Chorioptes* spp., *Saracoptes* spp., *Tarsonemus* spp., clover mite (*Bryobia praetiosa*), *Panonychus* spp., *Tetranychus* spp. (spider mites), *Raillietas* spp., *Pneumonyssus* spp., *Sternostorma* spp., *Acarapis* spp., *Cheyletiella* spp., *Myobia* spp., *Psorergates* spp., *Demodex* spp., *Trombicula* spp., *Listrophorus* spp., *Tyrophagus* spp., *Sarcoptes* spp., *Notoedres* spp., *Cytodides* spp., *Laminosioptes* spp.; and the like.

While the composition of the present invention has the excellent pesticidal activities against various species of pests, it shows particularly favorable efficacy for control of vector or nuisance pests including cockroaches such as German cockroach (*Blattella germanica*), smokybrown cockroach (*Periplaneta fuliqinosa*), American cockroach (*Periplaneta americana*), brown cockroach (*Periplaneta brunnea*) and oriental cockroach (*Blatta orientalis*), house mites such as mold mite (*Tyrophagus putrescentiae*), American house dust mite (*Dermatophagoides farinae*) and Cheyletid mites (*Chelacaropsis*), fleas such as cat flea (*Ctenocephalides felis*), mosquitos such as brown house mosquito (*Culex pipiens pallens*) and Asian tiger mosquito (*Aedes albopictus*), and flies such as housefly (*Musca domestica*), and wood pests including termites such as Formosan substerranean termite (*Copptotermes formosanus*), Japanese subterranean termite (*Reticulitermes speratus*), American common dry-wood termite (*Incistermes minor*), Daikoku dry-wood termite (*Cryptotermes domesticus*), *Odontotermes formosanus*, *Coptotermes formosanus*, *Reticulitermes speratus*, *R. flavipes*, *R. hesperus*, *R. virqinicus*, *R. tibialis*, *Incisitermes minor*, *Cryptotermes domesticus*, *Odontotermes formosanus*, and *Heterotermes aureus*, termite species of the families (and pest genera) Mastotermitidae (*Mastotermes* species), Hodotermididae (*Anacanthotermes*, *Zootermopsis* species), Rhinotermitidae (*Coptotermes*, *Heterotermes*, *Reticulitermes*, *Psammotermes*, *Prorhinotermes*, *Schedorhinotermes* species), Kalotermitidae (*Glyoptotermes*, *Neotermes*, *Cryptotermes*, *Incisitermes*, *Kalotermes*, *Marqinitermes* species), Serritermitidae, and Termitidae (*Pericapritermes*, *Allodontermes*, *Microtermes*, *Odontotermes*, *Nasutitermes*, *Termes*, *Amitermes*, *Globitermes*, *Microcerotermes* species), Termopsidae (*Hodotermopsis*, *Zootermopsis* species), and other pest species of termites, raw logvermin such as bark beetles (Scolytidae), longicorn beetles (Cerambycidae), weevils (Curculionidae), pinhole borers (Platypodidae) and horntails (Siricidae), and dry wood vermin such as powderpost beetle (*Lyctus brunneus*), false powderpost beetles (Bostrychidae), deathwatch and drugstore beetles (Anobiidae) and dry-wooden longicorn bettle (*Stromatium longicorne*).

An exemplary method for controlling pests comprises applying (such as by spraying) to a pest or site of pest infestation, a pesticidally effective amount of a pesticidal composition of the present invention in an amount sufficient to prevent infestation of the host and the composition does not damage the host's tissue. Of particular interest is use of the pesticide compositions of the invention in treating fungal infestations of fruit bearing plants such as strawberry plants. By treatment of a diseased plant with the composition of the invention in an amount sufficient to treat such a fungal infestation, pests such as powdery mildew can be controlled or eliminated, thus restoring the plant to a healthy state. Also of particular interest is use of the pesticide compositions of the invention in controlling arthropod infestations of ornamental plants such as roses. By treatment of a diseased plant with the composition of the invention in an amount sufficient to treat such a arthropod infestation, pests such as aphids and spider mites can be controlled or eliminated, thus restoring the plant to a healthy state.

Use of pesticides is regulated in the United States by the Environmental Protection Agency (EPA) under authority of the Federal Insecticide, Fungicide and Rodenticide Act (FIFRA). Tolerance for residues of pesticides in agricultural commodities are established by the (EPA) and enforced by the Food and Drug Administration (FDA) under authority of the Federal Food, Drug and Cosmetic Act (FD&C Act). This regulatory environment leads to another aspect of this invention, which is an article of manufacture. In this aspect a pesticidally active composition of the present invention is sold in a container that will be suitable for storing the composition for its shelf life. Associated with the container is printed instructions and/or a printed label indicating that the subject composition can be used to control pests, i.e., used as a pesticide and providing instructions for using the composition for pesticidal purposes in accordance with the treatment method set forth herein. The container may have associated with it a delivery device that allows the composition to be applied to the pest population or to the area to be treated. For liquid compositions this is generally a hand-operated, motorized or pressurized pressure-driven sprayer. The container may be made of any suitable material such as a polymer, glass, metal, or the like. Usually, the labeling is associated with the container by being adhered to the container, or accompanying the container in a package sold to the user. Such label may indicate that the composition is approved for use as a pesticide. The instructions will spell out the type of pests for which the pesticidal composition is to be used, the application method, the rate of application, dilution requirements, use precautions, and the like.

The efficacy of the pesticidal compositions of the present invention may be monitored by determining the mortality of or damage to the pest population, i.e., by determining its adverse effect upon treated pests. This includes damage to the pests, inhibition or modulation of pest growth, inhibition of pest reproduction by slowing or arresting its proliferation, or complete destruction/death of the pest, all of which are encompassed by the term "controlling". The term "pesticidally effective amount" is an amount of the compound of the invention, or a composition containing the compound, that has an adverse affect on at least 25% of the pests treated, more preferably at least 50%, most preferably at least 70% or greater. Preferably, an "effective pest-inhibiting amount" is an amount of the compound of the invention, or a composition containing the compound, where 25% or greater mortality against pests is achieved, preferably 50% or greater, more preferably 70% or greater mortality. Similarly, an "effective pest-growth modulating amount" is preferably one where 25% or greater pest-growth modulation is achieved, preferably 50% or greater, more preferably 70% of greater. The term "amount sufficient to prevent infestation" is also used herein and is intended to mean an amount that is sufficient to deter all but an insignificant sized pest population so that a disease or infected state is prevented. The actual value of a pesticidally effective amount for a given compound is preferably determined by routine screening procedures employed to evaluate pesticidal activity and efficacy, such as are well known by those skilled in the art and as are described in the Examples. It is expected that compounds of the invention having a higher level of pesticidal activity can be used in smaller amounts and concentrations, while those having a lower level of activity may require larger amounts or concentrations in order to achieve the same pesticidal effect. Efficacy is also monitored by phytotoxicity to the plants that are infested with the pest population, tissue damage to the host infected with the pest population and any adverse effects that might be experienced by a human user who is applying the composition to an infested plant or animal. Accordingly, the amount of composition or active compound used in the methods of the invention, meets the mortality, modulation or prevention criteria above, and preferably has minimal or no adverse effect on ornamental and agricultural plants (such as phytotoxicity), wildlife and humans that may come into contact with such compound.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE 1

Pesticidal Effects of Rosemary Oil and Wintergreen Oil

Studies were conducted to evaluate the individual toxicity, in terms of speed of action and mortality, of rosemary oil and wintergreen oil against American cockroaches, and then a blend of these two oils to determine if similar toxic effects could be obtained using a proprietary blend that was less expensive to produce and easier to employ in different end-use formulations. Methyl salicylate was used as wintergreen oil. American cockroaches were confined under a screened cap and then sprayed with approximately 3.7 grams of each test chemical using a trigger sprayer. Immediately after spraying, the insects were released into a large plastic container and observed for signs of toxicity. Three American cockroaches were used in each experiment. The times for immobilization (IM), knockdown (KD), and mortality were recorded for each test insect. An untreated control was provided. No mortality was observed in the control.

|  | IM | KD | Mortality |
|---|---|---|---|
| 100% Methyl Salicylate | — | 31 sec | >2 min |
|  | — | 1 m 35 sec | >2 min |
|  | 45 sec | — | >2 min |
| 100% Rosemary Oil | — | 10 sec | 1 m 15 sec |
|  | — | 10 sec | 1 m 46 sec |
|  | — | 48 sec | >2 min |
| 80% Methyl Salicylate 20% Rosemary Oil | — | 10 sec | 1 m 05 sec |
|  | — | 20 sec | 1 m 23 sec |
|  | — | 8 sec | 40 sec |

The above data demonstrates the fast action of rosemary oil in terms of both knockdown and mortality as compared to wintergreen oil. The study further demonstrates that a proprietary blend of rosemary oil with wintergreen oil will perform as well or better than rosemary oil by itself. The ratio of wintergreen oil to rosemary oil in this blend is 4:1.

EXAMPLE 2

Pesticidal Effects of Rosemary Oil and Wintegreen Oil with Mineral Oil Against Plant Pests A formulation (DR-A-034) consisting of 5% w/w rosemary oil, 22.5% w/w wintergreen oil, 22.5% w/w mineral oil, 0.5% w/w lecithin (emulsifier), and 49.5% w/w water was prepared and labeled Hexacide™. Hexacide™ was applied in dilute form at different rates per acre to the pests itemized below in various greenhouse and field studies. In all of these studies, positive controls consisting of conventional pesticides were utilized for comparative efficacy. In laboratory and greenhouse tests, the following exemplary pests were successfully controlled with HEXACIDE™.

| Common Name | Scientific Name |
|---|---|
| Boll Weevil | Anthonomus grandis |
| Colorado Potato Beetle | Leptinotarsa decemlineata |
| Green Peach Aphid | Myzus persicae |
| Potato Aphid | Macrosiphum euphorbiae |
| Strawberry Aphid | Chaetosiphos fragaefolii |
| Western Flower Thrips | Frankinelli occidentalis |
| Two Spotted Spidermite | Tetranychus urticae |
| Beet Armyworm | Spodoptera exigua |
| Blackheaded Fireworm | Rhopobota naevana |
| Cabbage Looper | Tricholplusea ni |
| Codling Moth | Cydia pomonella |
| Diamondback Moth | Plutella xylostella |
| Fall Armyworm | Spodoptera frugipetda |
| Oblique-Banded Leafroller | Choristoneura rosaceana |
| Silverleaf Whitefly | Bemisia argentifolii |
| Sweetpotato Weevil | Cylas fromicarius elegantulus |
| Tomato Pinworm | Keiferia lycoperscella |
| Tomato Fruitworm | Helicoverpa zea |
| Yellowstriped Armyworm | Spodoptera ornithogalli |

Efficacy

In greenhouse and field studies, HEXACIDE™ (DR-A-034) provided equivalent results to commercialy available chemical pesticide such as Talstar®, Avid®, Agri-Mek®, Kelthane®, Capture®, and Conserve®, (see Tables 1-11 and FIGS. 1-11). Table 1 below shows the effectiveness of HEXACIDE™ Against Green Peach Aphid *Myzus persicae* on Ornamental Sweet Potato *Lpomora batatas*.

TABLE 1

| | | | Number of Live Motiles | | | |
|---|---|---|---|---|---|---|
| Treatment | Rate/ 100 gal | Pre- treatment | 1 DAT | 2 DAT | 7 DAT | % Control |
| Untreated Control | / | 36 a | 34 a | 61 a | 67 a | / |
| HEXACIDE ™ | 64 oz | 45 a | 3 b | 0 b | 0 c | 100 |
| HEXACIDE ™ | 128 oz | 66 a | 2 b | 0 b | 1 c | 98.5 |
| HEXACIDE ™ | 256 oz | 39 a | 0 b | 0 b | 0 c | 100 |
| Talstar ® | 10 oz | 41 a | 10 b | 9 b | 29 b | 58.2 |
| LSD (P = 0.05) | | 52.4 | 8.3 | 16.9 | 18.3 | |
| SD | | 31.4 | 4.9 | 10.1 | 11 | |

Means followed by same letter do not significantly differ (p=0.05, Duncan's New MRT)

DAT: days after treatment

Latron B-1956 at 0.0625% v/v used as adjuvant

Three replicates per treatment

Table 2 below shows the effectiveness of HEXACIDE™ against the Green Peach Aphid (*Myzus persicae*) on Cotton.

TABLE 2

Means followed by same letter do not significantly
differ (p = 0.05, Duncan's New MRT)
DAT = days after treatment
Latron B-956 at 0.0625% v/v used as adjuvant
Three replicates per treatment. 125 GPA

|  | Rate | Number of Live Nymphs % Control (Pretreatment 1 DAT 2 DAT) | Number of Live Adults % Control (Pretreatment 1 DAT 2 DAT) |
|---|---|---|---|
| Untreated Control | 0 | 32.0 a | 25.3 a |
|  |  | 42.3 a | 26.8 a |
|  |  | 47.5 a | 27.0 a |
| HEXACIDE ™ | 256 oz | 37.0 a | 31.3 a |
|  |  | 0.8 a | 3.5 b |
|  |  | 3.0 b | 7.8 b |
|  |  | 93.6 | 71.1 |
| Talstar ® | 10 oz | 44.3 a | 33.0 a |
|  |  | 25.5 a | 12.3 ab |
|  |  | 6.0 b | 10.8 b |
|  |  | 87.4 | 61.8 |
| LSD (p = 0.05) |  | 38.5 | 23.7 |
|  |  | 46.3 | 16.6 |
|  |  | 33.3 | 12.2 |
| SD |  | 6.2 | 14.8 |
|  |  | 28.9 | 10.4 |
|  |  | 20.8 | 7.6 |

Table 3 below exemplifies the effectiveness of HEXACIDE™ against the strawberry aphid *Chaetosiphos fragaefoliion* on Strawberries. Means followed by same letter does not significantly differ (p=0.05 Duncan's New MRT). A randomized complete block design was used. 35 gallons per acre spray volume (GPA) was employed. DAT=Days After Treatment Four Replicates per treatment were performed.

TABLE 3

|  |  | Number of Live Aphids |  |  |  |  |
|---|---|---|---|---|---|---|
| Treatment | Rate/ Acre | Pre-treatment | 3 DAT | 7 DAT | 14 DAT | % Control |
| Untreated Control | / | 17.4 a | 16.9 a | 13.3 a | 21.0 a | / |
| HEXACIDE ™ | 1 qt | 17.4 a | 3.3 b | 1.2 b | 0.7 b | 96.6 |
| HEXACIDE ™ | 2 qt | 18.1 a | 2.7 b | 1.2 b | 0.5 b | 97.6 |
| HEXACIDE ™ | 4 qt | 15.5 a | 2.8 b | 1.1 b | 0.7 b | 96.7 |
| Capture ® | 4 oz | 16.2 a | 2.5 b | 0.8 b | 0.2 b | 99.0 |

Table 4 below exemplifies the effectiveness of HEXACIDE™ Against Greenhouse Whitefly *Trialurodes vaporariorum* on Poinsetta *Euphorbia puicherrima*. Means followed by same letter does not significantly differ (p=0.05 Duncan's New MRT). Results recorded 7 days after the second treatment. Latron B-1956 @ 0.0625% was used as an adjuvant. Eight replicates per treatment were performed.

TABLE 4

|  | Rate/ | Number of Live Insects (% Control) | | |
|---|---|---|---|---|
| Treatment | 100 gal | Nymphs | Pupae | Eggs |
| Untreated Control | / | 230.1 | 10.3 | 183.4 |
| HEXACIDE ™ | 32 oz | 48.5 (78.9%) | 5.1 (50.4%) | 71.6 (60.9%) |
| HEXACIDE ™ | 128 oz | 40.3 (82.5%) | 2.5 (75.7%) | 57.0 (63.5%) |
| Agri-Mek ® | 30 oz | 68.8 (70.1%) | 5.9 (42.7%) | 118.6 (35.3%) |
| LSD (p = 0.05) |  | 42.56 | 13.91 | 31.84 |
| SD |  | 41.56 | 13.58 | 31.09 |

Table 5 below shows the effectiveness of HEXACIDE™ Against Western Flower Thrip *Frankliniella occidentalis* on Marigold *Tagetes erecta*. Means followed by same letter do not significantly differ (p=0.05, Duncan's New MRT). DAT=days after treatment. Latron B-1956 at 0.0625% v/v used as an adjuvant. Three replicates per treatment were performed.

TABLE 5

|  | Rate/ | Number of Live Motiles | | |
|---|---|---|---|---|
| Treatment | 100 gal. | Pretreatment | 1 DAT | 3 DAT |
| Untreated Control | / | 8 a | 39 a | 17 a |
| HEXACIDE ™ | 128 oz | 11 a | 0 d | 8 b |
| Conserve ® | 6 fl oz | 12 a | 22 b | 1 c |
| LSD (p = 0.05) |  | 10.5 | 11.2 | 7.8 |
| SD |  | 6.2 | 6.7 | 4.7 |

Table 6 below shows the effectiveness of HEXACIDE™ Against Two-Spotted Spider Mite *Tetranychus urticae* on bell peppers. Means followed by same letter do not significantly differ (p=0.05, Duncan's New MRT). Four replicates per treatment were performed.

TABLE 6

|  |  | Number of Live Mites | | | |
|---|---|---|---|---|---|
| Treatment | Rate/ 100 gal | Pre-treatment | 5 DAT | 10 DAT | 15 DAT | % Control |
| Untreated Control | / | 62.0 a | 36.7 cc | 30.7 c | 9.8 b | / |
| HEXACIDE ™ | 120 oz | 55.7 a | 1.8 a | 0.5 a | 1.0 a | 89.7 |
| HEXACIDE ™ | 60 oz | 65.8 a | 4.3 a | 0.7 a | 1.2 a | 87.7 |
| Avid ® | 4 oz. | 62.2 a | 7.2 ab | 1.3 ab | 0.5 a | 94.8 |
| Tetrasan SWD | 16 oz | 59.5 a | 14.3 cd | 4.3 b | 0.3 a | 96.9 |

Table 7 below shows the effectiveness of HEXACIDE™ Against Two-Spotted Spider Mite *Tetranychus urticae* on Marigold *Tageies eroota*. Means followed by same letter do not significantly differ (p=0.05, Duncan's New MRT). DAT=days after treatment. Latron B-1956 at 0.065% v/v used as an adjuvant. Three replicates per treatment were performed.

TABLE 7

|  | Rate/ | Number of Live Motiles | | | |
|---|---|---|---|---|---|
| Treatment | 100 gal | Pre-treatment | 1 DAT | 3 DAT | 7 DAT | % Control |
| Untreated Control | / | 91.7 a | 165 a | 355 a | 370 a | / |
| HEXACIDE ™ | 16 oz | 144.3 a | 55 b | 89 b | 63 cd | 81.6 |
| HEXACIDE ™ | 32 oz | 87 a | 43.7 b | 96.7 b | 97 cd | 73.6 |
| HEXACIDE ™ | 64 oz | 59.3 a | 21.3 b | 32 b | 60 d | 83.7 |
| Avid ® | 2 oz | 110.6 a | 52 b | 77.7 b | 24.3 d | 93.4 |
| LSD (P = 0.05) |  | 127.2 | 53.9 | 124.6 | 92.6 |  |
| SD |  | 75.7 | 32.1 | 74.2 | 55.1 |  |

Table 8 below shows the effectiveness of HEXACIDE™ Against Two-Spotted Spider Mite *Tetranychus urticae* on Strawberries. Field Trials. Means followed by same letter does not significantly differ (p=0.05 Duncan's New MRT). Four replicates per treatment were performed.

TABLE 8

| Treatment | Rate/acre | Pre-treatment | Number of Live Mites | | | % Control |
| --- | --- | --- | --- | --- | --- | --- |
| | | | 3 DAT | 7 DAT | 14 DAT | |
| Untreated Control | / | 24.3 ab | 47.3 a | 19.8 a | 17.5 a | / |
| HEXACIDE ™ | 1 qt | 17 b | 31.3 bc | 5.3 b | 6.3 b | 64 |
| HEXACIDE ™ | 2 qt | 31.8 b | 28 bc | 1.5 b | 1.8 c | 89.7 |
| HEXACIDE ™ | 4 qt | 35.5 ab | 28 bc | 5.3 b | 1.5 c | 91.4 |
| Agri-Mek ® | 8 oz. | 24.3 ab | 35 b | 2.3 b | 5.8 bc | 66.8 |
| LSD (p = 0.05) | | 14.1 | 11.4 | 4.6 | 2.7 | |
| SD | | 9.59 | 7.7 | 3.2 | 1.8 | |

Table 9 below shows the effectiveness of HEXACIDE™ Against Two-Spotted Spider Mite *Tetranychus urticae* on Strawberry. A randomized complete block design was utilized. Four replicates per treatment (200 gallons spray volume per acre (GPA).) were performed utilizing.

TABLE 9

| Treatment | Rate/Acre | Number of Live Motiles | | | | | |
| --- | --- | --- | --- | --- | --- | --- | --- |
| | | Pre-treatment 6/8 | 6/15 | 6/22 | 6/29 | 7/5 | 7/12 |
| Untreated Control | / | 12.5 | 25.3 | 41.5 | 48.1 | 68.4 | 124.5 |
| HEXACIDE ™ | 4 qts | 3.9 | 3.6 | 5.9 | 7.8 | 21.6 | 34.9 |
| Agri-Mek ® | 32 oz | 17.2 | 10.1 | 7.6 | 11.2 | 8.6 | 22.1 |

Table 10 below shows the effectiveness of HEXACIDE™ Against Pacific Mite *Tetranychus pacificus* on grapes. Means followed by same letter do not significantly differ (p=0.05, Duncan's New MRT). DAT=days after treatment. Latron B-1956 @ 3 oz/acre used as an adjuvant. Four replicates per treatment were performed.

TABLE 10

| Treatment | Rate/Acre | Pre-treatment | Number of Live Mites | | | % Control |
| --- | --- | --- | --- | --- | --- | --- |
| | | | 2 DAT | 7 DAT | 14 DAT | |
| Untreated Control | / | 30.0 a | 18.0 a | 12.8 a | 9.0 a | / |
| HEXACIDE ™ | 3 qt | 28.8 a | 4.3 b | 2.5 b | 0.0 b | 100.0 |
| HEXACIDE ™ | 6 qt | 24.5 a | 4.8 b | 2.3 b | 1.3 b | 85.5 |
| Kelthane 200 | 2.5 lb | 23.5 a | 5.0 b | 3.8 b | 0.5 b | 94.4 |

Table 11 below shows the effectiveness of HEXACIDE™ Against Melon Aphids *Aphis gossypii* on squash. Means followed by same letters do not significantly differ (p=0.05). Randomized complete block design was used. Five replicates per treatment were performed. 100 gallons spray volume per acre (GPA). Latron CS-7 at 4 ml/gallon was added to all treatments. All foliar applied pesticidal compositions applied, except Admire and Platinum (soil insecticides). HEXACIDE™, Azadiractin and Pyganic applied three times at one week interval. Other products applied once.

TABLE 11

| Treatment | Rate/Acre | Mean % Aphids per Leaf | | |
| --- | --- | --- | --- | --- |
| | | Pretreatment | 6 DAT | 12 DAT |
| Untreated Conrol | / | 5.5 b | 7.8 d | 20.8 d |
| HEXACIDE ™ | 2 qt | 9.7 c | 2.8 b | 3.9 ab |
| Azadiractin | 1 qt | 3.9 b | 5.4 c | 15.1 c |
| Pyganic | 1 qt | 0.4 b | 3.1 b | 4.6 b |
| Fulfill | 77 g | 5.3 b | 0.1 a | 0.1 a |
| Admire | 170 g | 0.7 b | 0.4 b | 0.8 ab |
| Platinum | 78 g | 0.3 a | 0.3 a | 1.7 a |
| Actara | 86 g | 7.0 bc | 0 a | 0.1 a |
| Lannate | 454 g | 6.8 b | 0 a | 0.2 a |

The greenhouse and field studies itemized above demonstrate the invertebrate control observed at various stages of the lifecycle of plant pests. This extraordinary control is equivalent to that of conventional synthetic pesticides and is unexpected.

EXAMPLE 3

Pesticidal Effects Against Household Pests

Multiple studies were completed over the course of several months utilizing rosemary oil and wintergreen oil with and without various diluents as well as conventional pesticides. Insects were observed for immobilization (IM), knockdown (KD), and mortality. Special focus was given to speed of action of the test chemicals and ratios involved therein. Methyl salicylate (MS) was used as wintergreen oil.

Effect on American Cockroaches 24 hrs after arriving from supplier. Test procedure: Cockroaches are held under screened-cap for spray and then released in open container. Administered 4 squeezes of trigger spray (approximately 3 grams) of test chemical to insect unless otherwise noted. Insects are monitored for knockdown and mortality. Three insects were used per test chemical. EcoPCO AC™ was utilized as a positive control. Untreated controls were also utilized. No mortality was observed in the untreated controls. Results are shown in Table 12.

TABLE 12

| | KD | Mortality |
| --- | --- | --- |
| EcoPCO AC formulation | No KD | 58 s |
| | No KD | 1 m 07 s |
| | No KD | 6 m 07 s |
| 46 g Mineral oil | 2 m 30 s | >5 m |
| 40 g MS | 2 m 17 s | >5 m |
| | no KD | 2 m 20 s |
| 40% Mineral oil | no KD | 45 s |
| 40% MS | no KD | 30 s |
| 20% Rosemary | 14 s | 30 s |
| 70% Mineral oil | 27 s | 1 m 10 s |
| 30% MS | no KD | 43 s |
| | no KD | 4 m 05 s |
| 30% Mineral oil | no KD | >5 m |
| 70% MS | no KD | >5 m |
| | no KD | 1 m 56 s |
| 20% Mineral oil | 1 m 32 s | >5 m |
| 60% MS | 1 m 10 s | >5 m |
| 20% Rosemary | 1 m 21 s | >5 m |
| 50% MS | 4 m 30 s | >5 m |
| 50% Castor oil | no KD | >5 m |
| 25% MS | no KD | 38 s |
| 75% Rosemary | 8 s | 13 s |
| (*solution ate through glove) | no KD | 29 s |
| 50% MS | no KD | 28 s |
| 50% Rosemary | 16 s | 36 s |
| 75% MS | no KD | 24 s |
| 25% Rosemary | no KD | 42 s |
| 100% Mineral oil - 4 squeezes and release | no KD | >5 m |

TABLE 12-continued

|  | KD | Mortality |
|---|---|---|
| 100% Rosemary - 4 squeezes and release | no KD | 26 s |
| Note below effects when applied directly to thorax of insect using Pasteur Pipette: | | |
| 100% MS - 1 drop | 3 m 40 s | >5 m |
|  | no KD | >5 m |
|  | no KD | >5 m |
| 100% Mineral oil - 1 drop | KD @5 m 46 s | Mort >7 m |
| "gasping" at 1 m 40 s | | |
| very lethargic at 3 m | | |
| 100% Rosemary - 1 drop | KD @ 1 m 55 s | mort >5 m |
| neurotoxic signs at 48 s | | |

The data outlined above demonstrates the unique and unexpected efficacy both in terms of knockdown and mortality using rosemary oil and wintergreen oil. The data clearly indicates that a certain amount of mineral oil in combination with rosemary oil and wintergreen oil provides enhanced insecticidal effects using less active ingredients. Various ratios of the proprietary blend (rosemary oil, wintergreen oil, mineral oil) will create knockdown and mortality, but a more preferred blend is 40% wintergreen oil, 40% mineral oil, and 20% rosemary oil. Rosemary is very effective as a direct spray, and causes neurotoxic excitation upon contact, but is abrasive on surfaces and is also very expensive. Wintergreen oil is an effective neurotoxin for mortality and is relatively inexpensive, but is slow acting and has a strong fragrance. Mineral oil is odorless and provides excellent spreading properties over the surface of the insect, but is not neurotoxic to insects and has poor knockdown properties. Rosemary oil and wintergreen oil complement each other's beneficial toxic properties while providing fast acting pesticides that are affordable and aesthetically acceptable.

B) Effects on American Cockroaches. Test procedure: Cockroaches are held under screened-cap for spray and then released in open container. Administered 3 squeezes of trigger spray (approximately 2.2 grams) of test chemical (Table 13) to insect unless otherwise noted. Insects are monitored for knockdown and mortality. Three to five insects were used per test chemical. Untreated controls were utilized. No mortality was observed in the untreated controls. Results are shown in Table 14.

TABLE 13

|  | E51-1 | E51-2 | E51-3 | E51-4 | E51-5 | E51-6 | E51-7 | E51-8 | E51-9 |
|---|---|---|---|---|---|---|---|---|---|
| Mineral oil | 40% | 40% | 0 | 30% | 30% | 20% | 20% | 15% | 10% |
| MS | 40% | 40% | 50% | 50% | 55% | 60% | 55% | 60% | 65% |
| PEP | 20% | 0 | 20% | 15% | 10% | 15% | 15% | 15% | 15% |
| Cinnamon oil | 0 | 20% | 0 | 0 | 0 | 0 | 0 | 0 | 0 |
| Castor oil (yellow) | 0 | 0 | 30% | 0 | 0 | 0 | 0 | 0 | 0 |
| Rosemary | 0 | 0 | 0 | 5% | 0 | 5% | 5% | 5% | 5% |
| Sesame oil | 0 | 0 | 0 | 0 | 5% | 0 | 0 | 0 | 0 |
| Soybean oil | 0 | 0 | 0 | 0 | 0 | 0 | 5% | 5% | 5% |

PEP = 2-phenethyl propionate

TABLE 14

|  | IM | KD | Mortality |
|---|---|---|---|
| E51-1 | 29 s | no KD | 1 m 34 s |
|  |  | no KD | 38 s |
|  |  | no KD | 56 s |
|  |  | no KD | 35 s |
|  | 33 s | no KD | 2 m 09 s |
| *2 trigger sprays | 1 m 32 s | no KD | 1 m 47 s |
|  |  | no KD | >3 m |
|  |  | 1 m 16 s | >3 m |
|  |  | no KD | >3 m |
| E51-2 |  | 27 s | 1 m 26 s |
|  |  | no KD | 27 s |
|  |  | no KD | >3 m |
| E51-3 | 14 s | no KD | 28 s |
|  |  | no KD | >3 m |
|  |  | 49 s | 1 m 27 s |
|  |  | 29 s | 1 m 05 s |
| E51-4 |  | 7 s | 47 s |
|  |  | no KD | 1 m 13 s |
|  |  | 2 m 45 s | 2 m 50 s |
|  | 13 s | no KD | 1 m 02 s |
| *2 trigger sprays |  | 18 s | 1 m 15 s |
|  | 14 s | no KD | 44 s |
|  | 47 s | no KD | 1 m 42 s |
|  | 1 m 17 s | 1 m 35 s | >3 m |
|  | 36 s | no KD | 1 m 14 s |
| E51-5 |  | 3 m 00 s | >5 m |
|  |  | 57 s | >5 m |
|  |  | 1 m 07 s | >5 m |
| E51-6 | 16 s | no KD | 56 s |
|  |  | 1 m 15 s | >3 m |
|  | 9 s | no KD | 46 s |
|  | 22 s | no KD | 1 m 02 s |
| *2 trigger sprays |  | 40 s | 1 m 32 s |
|  | 20 s | no KD | 57 s |
|  | 15 s | no KD | 58 s |
| E51-7 | 16 s | no KD | 31 s |
|  | 15 s | no KD | 52 s |
|  | 32 s | No KD | 42 s |
|  |  | 6 s | 43 s |
| *2 trigger sprays | 25 s | no KD | 1 m 10 s |
|  |  | 10 s | 56 s |
|  | 41 s | 1 m 07 s | >3 m (3 m 24 s) |
|  |  | 1 m 27 s | >3 m |
| E51-8 |  | 1 m 19 s | >3 m |
|  | 1 m 27 s | 2 m 30 s | >3 m |
|  |  | 10 s | 48 s |
|  |  | 29 s | 1 m 02 s |
|  | 1 m 09 s | 2 m 29 s | >3 m |
| *2 trigger sprays |  | no KD | >3 m |
|  | 58 s | no KD | 2 m 02 s |
|  |  | 1 m 30 s | >3 m |
| E51-9 | 52 s | no KD | 3 m 26 s |
|  | 11 s | no KD | 46 s |
|  | 15 s | no KD | 1 m |
|  | 14 s | no KD | 48 s |
| *2 trigger sprays | 10 s | no KD | 2 m 33 s |
|  | 14 s | no KD | 1 m 14 s |
|  | 1 m 18 s | no KD | >3 m |

TABLE 14-continued

|  | IM | KD | Mortality |
|---|---|---|---|
|  | 13 s | no KD | 1 m 00 s |
|  |  | 2 m 20 s | >3 m |
|  | 55 s | no KD | 2 m 25 s |
| 40% MS | 1 m 43 s | no KD | >3 m |
| 40% Mineral Oil | 15 s | no KD | 54 s |
| 20% Rosemary | 17 s | no KD | 58 s |
| (3-blend) | 16 s | no KD | 33 s |
| *2 trigger sprays |  | 11 s | 39 s |
| adl2-4-122a |  | no KD | >3 m |
| (25% 3-blend in water) |  | no KD | >3 m |
|  |  | no KD | >3 m |
| adl2-4-122b | 31 s | no KD | 52 s |
| (50% 3-blend in water) | 27 s | no KD | 49 s |
|  | 1 m 23 s | 1 m 31 s | >3 m |
|  | 37 s | no KD | 1 m 12 s |

The data presented above exhibits the necessity of rosemary oil to offer fast action. Further, the data demonstrates the ability to add various diluents such as mineral oil, soybean oil and sesame oil, as well as various conventional pesticides such as 2-phenethyl propionate, to create desirable formulations containing rosemary oil and wintergreen oil. Several formulations perform quite well at higher dosage rates, but the proprietary blend of rosemary oil and wintergreen oil with mineral oil (3-blend) is most toxic at lower dosage rates. The speed of action in terms of immobilization and mortality are unexpected and offer distinct safety advantages over other conventional synthetic pesticides.

C) Testing performed on American Cockroaches. Test procedure: Cockroaches are held under screened-cap for spray and then released in open container. Administered 2 squeezes of trigger spray (approximately 1.5 grams) of test chemical (Table 15) to insect unless otherwise noted. Insects are monitored for knockdown and mortality. Two insects were used per test chemical. Untreated controls were utilized. No mortality was observed in the untreated controls. Results are shown in Table 16.

TABLE 15

|  | 001012-1 | 001012-2 | 001012-3 |
|---|---|---|---|
| PEP | 20% | 15% | 0 |
| Eugenol | 0 | 5% | 20% |
| Sesame oil | 5% | 0 | 5% |
| Soybean oil | 5% | 5% | 5% |
| MS | 35% | 40% | 35% |
| Safflower oil | 35% | 35% | 35% |

TABLE 16

|  | IM | KD | Mortality |
|---|---|---|---|
| 001012-1 | 40 s | — | 51 s |
|  | — | 2 m 28 s | >3 m |
| 001012-2 | 21 s | — | 54 s |
|  | — | 22 s | 44 s |
| 001012-3 | 15 s | — | 39 s |
|  | 2 m 05 s | 2 m 40 s | >3 m |

Testing on German Cockroaches sprayed with 1-trigger spray in large open container. Three insects per test chemical. Test chemicals identified above. Results are shown in Table 17.

TABLE 17

|  | IM | KD | Mortality |
|---|---|---|---|
| E51-4 | 12 s | — | 32 s |
|  | — | 19 s | 32 s |
|  | 28 s | — | 42 s |
| E51-6 | 11 s | — | 17 s |
|  | 13 s | — | 18 s |
|  | 15 s | — | 17 s |
| E51-9 | 4 s | — | 19 s |
|  | — | 8 s | 15 s |
|  | 9 s | — | 17 s |
| 3-blend | 6 s | — | 15 s |
|  | — | 9 s | 15 s |
|  | — | 9 s | 15 s |
| 001012-1 | — | 5 s | 15 s |
|  | 9 s | — | 20 s |
|  | — | 12 s | 30 s |
| 001012-2 | — | 12 s | 37 s |
|  | 20 s | — | 30 s |
|  | — | 28 s | 33 s |
| (fine mist) | 48 s | — | 2 m 10 s |
| (walk-across) | — | 22 s | 1 m 20 s |
| 001012-3 | — | 10 s | 32 s |
|  | — | 1 m 04 s | 1 m 14 s |
|  | — | 42 s | 2 m 42 s |

This data shows that German cockroaches are highly sensitive to pesticidal compositions of the present invention, requiring less dosage rates, even on walk across exposure trials.

Testing of houseflies sprayed 1-trigger spray into jar.

| E51-9 | 12/12 instant KD and mortality <30 s |
|---|---|
|  | 17/17 instant KD and mortality <30 s |

Testing performed on American Cockroaches. Test procedure: Cockroaches are held under screened-cap (with 10×10 cm plastic matting) for spray and then released in open container. Administered 2 squeezes of trigger spray (approximately 1.5 grams) of test chemical (Tables 18 and 19) to insect unless otherwise noted. Insects are monitored for knockdown and mortality. Two to six insects were used per test chemical. Untreated controls were utilized. No mortality was observed in the untreated controls. Results shown in Table 20.

TABLE 18

| E51-9B = 001018-4 | E51-9C | 001012-3A |
|---|---|---|
| 15% PEP | 15% Thyme oil | 15% Eugenol |
| 5% RM | 5% RM | 5% Sesame oil |
| 50% MS | 50% MS | 5% Soybean oil |
| 25% Mineral oil | 25% mineral oil | 50% MS |
|  |  | 20% Mineral oil |

TABLE 19

|  | 001027-1 | 001027-2 | 001027-3 | 001027-4 | 001027-5 | 001027-6 |
|---|---|---|---|---|---|---|
| PEP | 15% | 15% | 20% |  |  | 15% |
| Eugenol | 5% | — | — | 20% | — | — |
| Rosemary | — | 5% | — | — | 5% | 5% |

TABLE 19-continued

|  | 001027-1 | 001027-2 | 001027-3 | 001027-4 | 001027-5 | 001027-6 |
|---|---|---|---|---|---|---|
| Soybean oil | — | — | — | — | — | 5% |
| MS | 50% | 50% | 50% | 50% | 50% | 50% |
| Safflower oil | 20% | 20% | 20% | 20% | 20% | 15% |
| Mineral oil | — | 10% | 10% | 10% | 10% | 10% |
| Thyme oil | — | — | — | — | 15% | — |

TABLE 20

|  | IM | KD | Mortality |
|---|---|---|---|
| E51-9B (=001018-4) | 9 s | 15 s | 33 s |
|  | — | 38 s | 50 s |
|  | — | 15 s | 1 m 07 s |
|  | 11 s | — | 34 s |
| E51-9C | — | 7 s | 15 s |
|  | — | 5 s | 18 s |
|  | — | 17 s | 42 s |
| 001012-3A | — | 10 s | 21 s |
|  | 50 s | 1 m 10 s | 1 m 40 s |
|  | 27 s | — | 1 m 01 s |
|  | — | 53 s | 1 m 11 s |
| 001027-1 | — | — | >2 m |
|  | — | 20 s | 44 s |
|  | — | 15 s | 33 s |
|  | — | — | >2 m |
|  | 13 s | 17 s | 25 s |
|  | 10 s | — | 26 s |
| 001027-2 | 19 s | 33 s | 1 m 18 s |
|  | — | 16 s | 28 s |
|  | 10 s | 18 s | 25 s |
|  | 16 s | — | 30 s |
| 001027-3 | — | 11 s | 37 s |
|  | — | 12 s | 46 s |
|  | 16 s | 21 s | 42 s |
|  | 10 s | — | 29 s |
| 001027-4 | — | 29 s | 44 s |
|  | — | 6 s | 24 s |
|  | 28 s | 47 s | 1 m 11 s |
|  | — | 11 s | 28 s |
| 001027-5 | 11 s | — | 23 s |
|  | 47 s | 1 m 07 s | 1 m 28 s |
|  | — | 12 s | 29 s |
|  | — | 6 s | 25 s |
| 001027-6 (1-spray) | — | — | >2 m |
|  | 12 s | 19 s | 45 s |
|  | 7 s | — | 31 s |
|  | — | 12 s | 30 s |
|  | 12 s | — | 25 s |

The data presented above demonstrates the speed at which pesticidal compositions of the present invention act.

EXAMPLE 4

The following formulation (DR-A-041) was tested as an effective broad foliar fungicide in agriculture, vegetable, fruits, turf and ornamentals:

| Rosemary Oil | 16.36% w/w |
|---|---|
| Wintergreen Oil | 73.64% w/w |
| Rhodafac RE 610 | 10.00% w/w |

Figure 12:
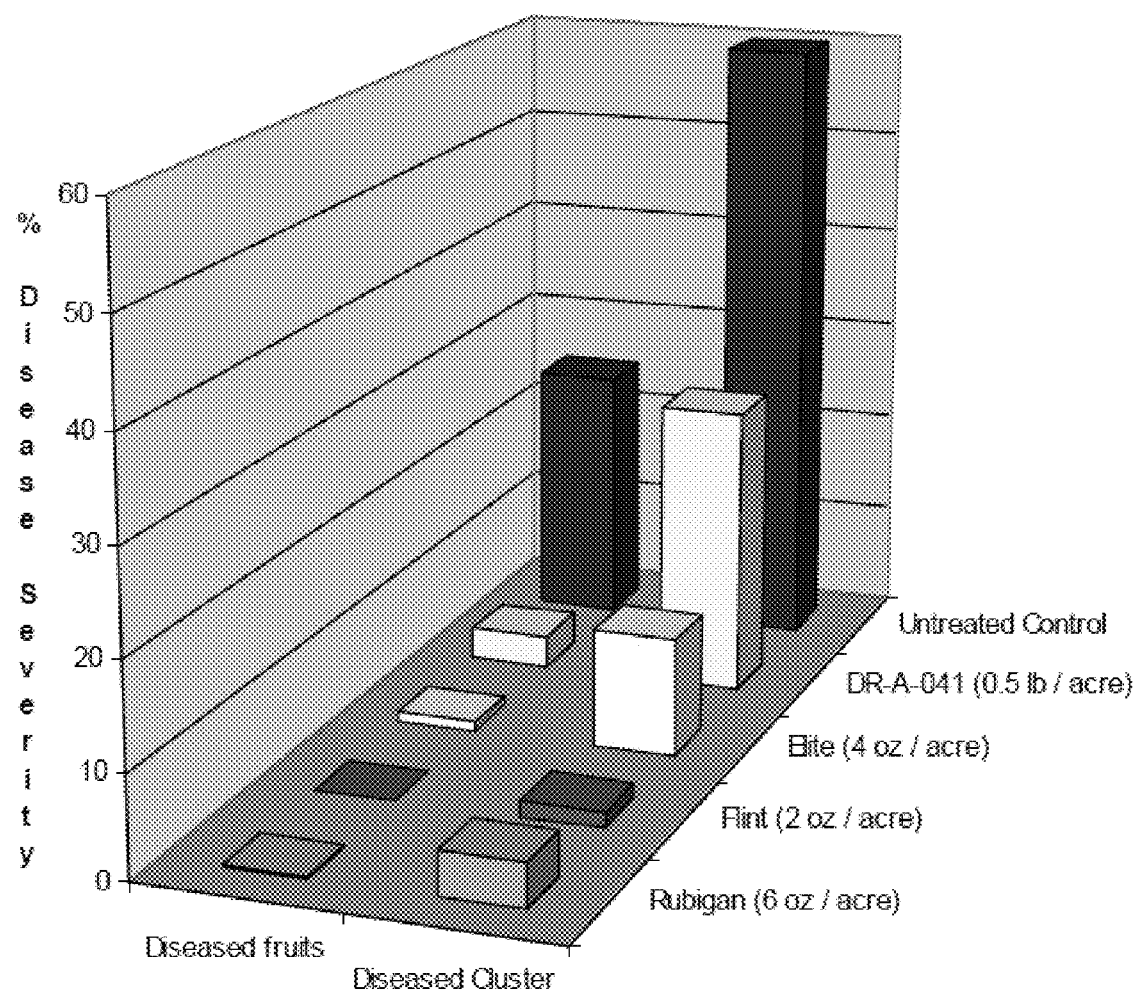
FIG. 12 depicts data obtained from a comparison of the broad foliar fungicidal activities of DR-A-041 and Rhodafac RE 610.

(Rhodafac RE 610 is sold by Rhodia, Cranbury N.J.). The results are shown in Tables 21-23 and FIG. 12.

Table 21 shows the effectiveness of DR-A-041 Experimental Fungicide Against Powdery Mildew *Uncinula necator* on Grapes. Randomized complete block design, 3 replicates, 4-5 applications/treatment @ 14-21 days intervals during pre-bloom to veraison 125 gallons spray volume/acre (GPA). Means followed by the same letter are not significantly different according to Fisher LSD t-test at p=0.05. Results were Log (x+1) transformed prior to statistical analysis due to heterogeneity of variance.

TABLE 21

| Treatment | Rate/Acre | % Average Disease Severity on fruits | % Diseased Cluster |
|---|---|---|---|
| Untreated Control | / | 24.9 a | 60.0 a |
| DR-A-041 | 0.5 lb | 3.2 ab | 28.1 b |
| Elite | 4 oz | 0.9 bc | 11.4 c |
| Rubigan | 6 oz | 0.2 c | 4.2 d |
| Flint | 2 oz | 0.03 dc | 1.5 dc |

Table 22 shows the effectiveness of DR-A-041 Experimental Fungicide Against Brown Patch *Rhizoctonia solani* on Turf. Field Tests. Means followed by the same letters are not significantly different at 0.05 level. Randomized complete block design, 4 replicates.

TABLE 22

| Treatment | Rate/1000 sq. ft | Plot Diseased Severity: 0 (no disease)-5 (>50% diseased) | | |
|---|---|---|---|---|
|  |  | June 27 | July 11 | July 24 |
| Untreated Control | / | 1.3 a | 3.5 a | 3.8 a |
| DR-A-041 | 2.0 oz | 2.3 a | 0.3 bc | 0.3 bc |
| Eagle G | 8.0 oz | 2.3 a | 1.5 bc | 2.5 a |
| Banner MAXX | 2.0 oz | 1.0 a | 0 c | 0 c |
| Daconil 82.5 WDG | 3.2 oz | 1.0 a | 0 c | 0.5 bc |
| Banner MAXX 1.3 MEC + Primo MAXX | 1.0 oz + 2.0 oz | 1.3 a | 0 c | 0.3 bc |

Table 23 shows the effectiveness of DR-A-041 Experimental Fungicide Against Dollar Spot *Sclerotinia homoeocarpa* on Turf. Means followed by the same letters are not significantly different at 0.05 level. Randomized complete block design, 4 replicates.

TABLE 23

| Treatment | Rate/1000 sq. ft | % Plot Diseased Severity | | |
|---|---|---|---|---|
|  |  | June 27 | July 11 | July 24 |
| Untreated Control | / | 3.3 a | 10.3 b | 9.3 ab |
| DR-A-041 | 2.0 oz | 4.5 a | 2.3 d | 0.8 c |
| Eagle G | 8.0 oz | 12.5 a | 20.1 a | 14.0 a |
| Banner MAXX | 2.0 oz | 2.5 a | 7.5 bd | 8.1 ab |
| Daconil 82.5 WDG | 3.2 oz | 8.9 a | 1.2 d | 0 c |
| Banner MAXX 1.3 MEC + Primo MAXX | 1.0 oz + 2.0 oz | 1.3 a | 0 c | 0.3 bc |

As can be seen from the above discussion, the pesticidal combinations of active compounds according to the present invention are markedly superior to known pesticidal agents/active compounds conventionally used for control of invertebrate pests.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A spray container consisting essentially of:
   rosemary oil in an amount of from 0.001 to 2% by weight,
   peppermint oil in an amount of from 0.001 to 2% by weight,
   cinnamon oil in an amount of from 0.001 to 2% by weight,
   sesame oil in an amount of from 0.001 to 2% by weight,
   thyme oil in an amount of from 0.001 to 2% by weight,
   soybean oil in an amount of from 0.0001 to 10% by weight, and
   wintergreen oil in an amount of from 0.0001 to 10% by weight.

2. The spray container of claim 1 further consisting essentially of at least one member selected from the group consisting of bentonite, calcium carbonate, cellulose, clove, dolomite, kaolin, lecithin, mustard and water.

3. The spray container of claim 1 further consisting essentially of at least one member selected from the group consisting of mineral oil, benzyl alcohol, citronellal, d-limonene and safflower oil.

* * * * *